United States Patent [19]
Young et al.

[11] Patent Number: 6,153,190
[45] Date of Patent: *Nov. 28, 2000

[54] ERYTHROPOIETIN RECEPTOR ANTIBODIES

[76] Inventors: Peter Ronald Young; Connie L. Erickson-Miller, both of SmithKline Beecham Corporation Corporate Intellectual Property - UW2220 P.O. Box 1539, King of Prussia, Pa. 19406-0939

[*] Notice: This patent issued on a continued prosecution application filed under 37 CFR 1.53(d), and is subject to the twenty year patent term provisions of 35 U.S.C. 154(a)(2).

[21] Appl. No.: 08/776,511

[22] PCT Filed: Jun. 7, 1996

[86] PCT No.: PCT/US96/09613

§ 371 Date: Jan. 28, 1997

§ 102(e) Date: Jan. 28, 1997

[87] PCT Pub. No.: WO96/40231

PCT Pub. Date: Dec. 19, 1996

Related U.S. Application Data

[63] Continuation-in-part of application No. 08/474,673, Jun. 7, 1995, abandoned.

[51] Int. Cl.[7] .......................... A61K 39/395; C12N 5/12; C12P 21/08; C07K 16/28
[52] U.S. Cl. ................... 424/141.1; 435/325; 435/334; 530/388.1
[58] Field of Search .................. 530/387.1, 387.3, 530/388.1, 388.23, 389.1, 389.2, 389.6; 424/141.1; 435/325, 334

[56] References Cited

FOREIGN PATENT DOCUMENTS

| 9008822 | 8/1990 | WIPO . |
| 9221029 | 11/1992 | WIPO . |

OTHER PUBLICATIONS

Callan et al., *PNAS USA vol. 90*, pp. 10454–10458, 1993.
J. Immunol., vol. 142, No. 3, Feb. 1, 1989, Schreurs et al., A *monoclonal antibody with IL–3 like acitivity blocks IL–3 binding and stimulates tyrosine phosphorylation* pp. 819–825.
Blood, vol. 82, No. 6, Sep. 15, 1993 Yet et al. *The extracytoplasmic domain of the erythropoietin receptor forms a monomeric complex with erythropoietin* pp.1713–1719.
Science, vol. 256, Jun. 19, 1992 Fuh et al. *Rational design of potent antagonist to the human growth hormone receptor* pp.1677–1680.
Proc. Natl. Acad. Sci USA vol. 89 Mar. 1992 Watowich et al. *Homodimerization and constitutive activation of the erythropoientin receptor* pp.2140–2144.
Blood, vol. 82, No. 1, Jul. 1, 1993 D'Andrea et al. *Anti–erthropoientin receptor antibodies inhibit erythropoietin binding and neutralize bioactivity* pp. 46–52.
J. Immunol., vol. 140, No. 2, Jan., 1992, Sugawara et al., *monoclonal antibodies with interleukin–3 like acitivity derived from a MRL/lpr mouse* pp. 526–530.

*Primary Examiner*—Gary L. Kunz
*Assistant Examiner*—Stephen Gucker
*Attorney, Agent, or Firm*—Kirk Baumeister; William T. King

[57] ABSTRACT

Monoclonal antibodies to the erythropoietin receptor are disclosed.

2 Claims, 16 Drawing Sheets plasmid mtalsEpoRFc    [SEQ ID NO: 1 and 2]

| | | | | |
|---|---|---|---|---|
| TCGCGCGTTT | CGGTGATGAC | GGTGAAAACC | TCTGACACAT | GCAGCTCCCG | 50 |
| GAGACGGTCA | CAGCTTGTCT | GTAAGCGGAT | GCCGGGAGCA | GACAAGCCCG | 100 |
| TCAGGGCGCG | TCAGCGGGTG | TTGGCGGGTG | TCGGGGCTGG | CTTAACTATG | 150 |
| CGGCATCAGA | GCAGATTGTA | CTGAGAGTGC | ACCATATGCG | GTGTGAAATA | 200 |
| CCGCACAGAT | GCGTAAGGAG | AAAATACCGC | ATCAGGCGCC | ATTCGCCATT | 250 |
| CAGGCTGCGC | AACTGTTGGG | AAGGGCGATC | GGTGCGGGCC | TCTTCGCTAT | 300 |
| TACGCCAGCT | GGCGAAAGGG | GGATGTGCTG | CAAGGCGATT | AAGTTGGGTA | 350 |
| ACGCCAGGGT | TTTCCCAGTC | ACGACGTTGT | AAAACGACGG | CCAGTGCCAG | 400 |
| TGAATTCGTT | GCAGGACAGG | ATGTGGTGCC | CGATGTGACT | AGCTCTTTGC | 450 |
| TGCAGGCCGT | CCTATCCTCT | GGTTCCGATA | AGAGACCCAG | AACTCCGGCC | 500 |
| CCCCACCGCC | CACCGCCACC | CCCATACATA | TGTGGTACGC | AAGTAAGAGT | 550 |
| GCCTGCGCAT | GCCCCATGTG | CCCCACCAAG | AGTTTTGCAT | CCCATACAAG | 600 |
| TCCCCAAAGT | GGAGAACCGA | ACCAATTCTT | CGCGGGCAGA | ACAAAAGCTT | 650 |
| CTGCACACGT | CTCCACTCGA | ATTTGGAGCC | GGCCGGCGTG | TGCAAAAGAG | 700 |
| GTGAATCGAA | CGAAAGACCC | GTGTGTAAAG | CCGCGTTTCC | AAAATGTATA | 750 |
| AAACCGAGAG | CATCTGGCCA | ATGTGCATCA | GTTGTGGTCA | GCAGCAAAAT | 800 |
| CAAGTGAATC | ATCTCAGTGC | AACTAAAGGG | GGGATCCGAT | ATCCAAGGTT | 850 |
| ACCGCGGACT | AGTCTAGTAA | CGGCCGCCAG | TGTGCTGGAA | TTCGGCT ATG | 900 |
| | | | | Met |
| | | | | 1 |

| GAC | CAC | CTC | GGG | GCG | TCC | CTC | TGG | CCC | CAG | GTC | GGC | TCC | CTT | 942 |
|---|---|---|---|---|---|---|---|---|---|---|---|---|---|---|
| Asp | His | Leu | Gly | Ala | Ser | Leu | Trp | Pro | Gln | Val | Gly | Ser | Leu | |
| | | 5 | | | | | 10 | | | | | | 15 | |

| TGT | CTC | CTG | CTC | GCT | GGG | GCC | GCC | TGG | GCG | CCC | CCG | CCT | AAC | 984 |
|---|---|---|---|---|---|---|---|---|---|---|---|---|---|---|
| Cys | Leu | Leu | Leu | Ala | Gly | Ala | Ala | Trp | Ala | Pro | Pro | Pro | Asn | |
| | | | | 20 | | | | | 25 | | | | | |

| CTC | CCG | GAC | CCC | AAG | TTC | GAG | AGC | AAA | GCG | GCC | TTG | CTG | GCG | 1026 |
|---|---|---|---|---|---|---|---|---|---|---|---|---|---|---|
| Leu | Pro | Asp | Pro | Lys | Phe | Glu | Ser | Lys | Ala | Ala | Leu | Leu | Ala | |
| 30 | | | | | 35 | | | | | 40 | | | | |

FIG. 7A

| | | | | | | | | | | | | |
|---|---|---|---|---|---|---|---|---|---|---|---|---|
| GCC | CGG | GGG | CCC | GAA | GAG | CTT | CTG | TGC | TTC | ACC | GAG | CGG | TTG | 1068 |
| Ala | Arg | Gly | Pro | Glu | Glu | Leu | Leu | Cys | Phe | Thr | Glu | Arg | Leu |
| | 45 | | | | 50 | | | | | 55 | | |

GCC CGG GGG CCC GAA GAG CTT CTG TGC TTC ACC GAG CGG TTG    1068
Ala Arg Gly Pro Glu Glu Leu Leu Cys Phe Thr Glu Arg Leu
    45              50                  55

GAG GAC TTG GTG TGT TTC TGG GAA GCG GCG AGC GCT GGG    1110
Glu Asp Leu Val Cys Phe Trp Glu Glu Ala Ala Ser Ala Gly
        60              65                  70

GTG GGC CCG GGC AAC TAC AGC TTC TCC TAC CAG CTC GAG GAT    1152
Val Gly Pro Gly Asn Tyr Ser Phe Ser Tyr Gln Leu Glu Asp
            75              80                  85

GAG CCA TGG AAG CTG TGT CGC CTG CAC CAG GCT CCC ACG GCT    1194
Glu Pro Trp Lys Leu Cys Arg Leu His Gln Ala Pro Thr Ala
                90                  95

CGT GGT GCG GTG CGC TTC TGG TGT TCG CTG CCT ACA GCC GAC    1236
Arg Gly Ala Val Arg Phe Trp Cys Ser Leu Pro Thr Ala Asp
100             105                 110

ACG TCG AGC TTC GTG CCC CTA GAG TTG CGC GTC ACA GCA GCC    1278
Thr Ser Ser Phe Val Pro Leu Glu Leu Arg Val Thr Ala Ala
    115                 120                 125

TCC GGC GCT CCG CGA TAT CAC CGT GTC ATC CAC ATC AAT GAA    1320
Ser Gly Ala Pro Arg Tyr His Arg Val Ile His Ile Asn Glu
        130                 135                 140

GTA GTG CTC CTA GAC GCC CCC GTG GGG CTG GTG GCG CGG TTG    1362
Val Val Leu Leu Asp Ala Pro Val Gly Leu Val Ala Arg Leu
            145                 150                 155

GCT GAC GAG AGC GGC CAC GTA GTG TTG CGC TGG CTC CCG CCG    1404
Ala Asp Glu Ser Gly His Val Val Leu Arg Trp Leu Pro Pro
                160                 165

CCT GAG ACA CCC ATG ACG TCT CAC ATC CGC TAC GAG GTG GAC    1446
Pro Glu Thr Pro Met Thr Ser His Ile Arg Tyr Glu Val Asp
170             175                 180

GTC TCG GCC GGC AAC GGC GCA GGG AGC GTA CAG AGG GTG GAG    1488
Val Ser Ala Gly Asn Gly Ala Gly Ser Val Gln Arg Val Glu
    185                 190                 195

ATC CTG GAG GGC CGC ACC GAG TGT GTG CTG AGC AAC CTG CGG    1530
Ile Leu Glu Gly Arg Thr Glu Cys Val Leu Ser Asn Leu Arg
        200                 205                 210

GGC CGG ACG CGC TAC ACC TTC GCC GTC CGC GCG CGT ATG GCT    1572
Gly Arg Thr Arg Tyr Thr Phe Ala Val Arg Ala Arg Met Ala
            215                 220                 225

FIG. 7B

```
GAG CCG AGC TTC GGC GGC TTC TGG AGC GCC TGG TCG GAG CCT    1614
Glu Pro Ser Phe Gly Gly Phe Trp Ser Ala Trp Ser Glu Pro
                230             235

GTG TCG CTG CTG ACG CCT AGC GAC CTG GAC CCC ATT GAG GGC    1656
Val Ser Leu Leu Thr Pro Ser Asp Leu Asp Pro Ile Glu Gly
240             245             250

CGT GGT ACC GAG CCC AAA TCG GCC GAC AAA ACT CAC ACA TGC    1698
Arg Gly Thr Glu Pro Lys Ser Ala Asp Lys Thr His Thr Cys
    255             260             265

CCA CCG TGC CCA GCA CCT GAA CTC CTG GGG GGA CCG TCA GTC    1740
Pro Pro Cys Pro Ala Pro Glu Leu Leu Gly Gly Pro Ser Val
        270             275             280

TTC CTC TTC CCC CCA AAA CCC AAG GAC ACC CTC ATG ATC TCC    1782
Phe Leu Phe Pro Pro Lys Pro Lys Asp Thr Leu Met Ile Ser
            285             290             295

CGG ACC CCT GAG GTC ACA TGC GTG GTG GTG GAC GTG AGC CAC    1824
Arg Thr Pro Glu Val Thr Cys Val Val Val Asp Val Ser His
                300             305

GAA GAC CCT GAG GTC AAG TTC AAC TGG TAC GTG GAC GGC GTG    1866
Glu Asp Pro Glu Val Lys Phe Asn Trp Tyr Val Asp Gly Val
310             315             320

GAG GTG CAT AAT GCC AAG ACA AAG CCG CGG GAG GAG CAG TAC    1908
Glu Val His Asn Ala Lys Thr Lys Pro Arg Glu Glu Gln Tyr
    325             330             335

AAC AGC ACG TAC CGG GTG GTC AGC GTC CTC ACC GTC CTG CAC    1950
Asn Ser Thr Tyr Arg Val Val Ser Val Leu Thr Val Leu His
        340             345             350

CAG GAC TGG CTG AAT GGC AAG GAG TAC AAG TGC AAG GTC TCC    1992
Gln Asp Trp Leu Asn Gly Lys Glu Tyr Lys Cys Lys Val Ser
            355             360             365

AAC AAA GCC CTC CCA GCC CCC ATC GAG AAA ACC ATC TCC AAA    2034
Asn Lys Ala Leu Pro Ala Pro Ile Glu Lys Thr Ile Ser Lys
                370             375

GCC AAA GGG CAG CCC CGA GAA CCA CAG GTG TAC ACC CTG CCC    2076
Ala Lys Gly Gln Pro Arg Glu Pro Gln Val Tyr Thr Leu Pro
380             385             390

CCA TCC CGG GAT GAG CTG ACC AAG AAC CAG GTC AGC CTG ACC    2118
Pro Ser Arg Asp Glu Leu Thr Lys Asn Gln Val Ser Leu Thr
    395             400             405
```

FIG. 7C

```
TGC CTG GTC AAA GGC TTC TAT CCC AGC GAC ATC GCC GTG GAG      2160
Cys Leu Val Lys Gly Phe Tyr Pro Ser Asp Ile Ala Val Glu
        410             415             420

TGG GAG AGC AAT GGG CAG CCG GAG AAC AAC TAC AAG ACC ACG      2202
Trp Glu Ser Asn Gly Gln Pro Glu Asn Asn Tyr Lys Thr Thr
            425             430             435

CCT CCC GTG CTG GAC TCC GAC GGC TCC TTC TTC CTC TAC AGC      2244
Pro Pro Val Leu Asp Ser Asp Gly Ser Phe Phe Leu Tyr Ser
                440             445

AAG CTC ACC GTG GAC AAG AGC AGG TGG CAG CAG GGG AAC GTC      2286
Lys Leu Thr Val Asp Lys Ser Arg Trp Gln Gln Gly Asn Val
450             455             460

TTC TCA TGC TCC GTG ATG CAT GAG GCT CTG CAC AAC CAC TAC      2328
Phe Ser Cys Ser Val Met His Glu Ala Leu His Asn His Tyr
    465             470             475

ACG CAG AAG AGC CTC TCC CTG TCT CCG GGT AAA TGAGTGTAGT       2371
Thr Gln Lys Ser Leu Ser Leu Ser Pro Gly Lys
            480             485

CTAGAAGCTT ACGCGTAGGC CTGAGCTCGC TGATCAGCCT CGAGGATCCA       2421

GACATGATAA GATACATTGA TGAGTTTGGA CAAACCACAA CTAGAATGCA       2471

GTGAAAAAAA TGCTTTATTT GTGAAATTTG TGATGCTATT GCTTTATTTG       2521

TAACCATTAT AAGCTGCAAT AAACAAGTTA ACAACAACAA TTGCATTCAT       2571

TTTATGTTTC AGGTTCAGGG GGAGGTGTGG GAGGTTTTTT AAAGCAAGTA       2621

AAACCTCTAC AAATGTGGTA TGGCTGATTA TGATCAGTCG ACCGATGCCC       2671

TTGAGAGCCT TCAACCCAGT CAGCTCCTTC CGGTGGGCGC GGGGCATGAC       2721

TATCGTCGCC GCACTTATGA CTGTCTTCTT TATCATGCAA CTCGTAGGAC       2771

AGGTGCCGGC AGCGCTCTGG GTCATTTTCG GCGAGGACCG CTTTCGCTGG       2821

AGCGCGACGA TGATCGGCCT GTCGCTTGCG GTATTCGGAA TCTTGCACGC       2871

CCTCGCTCAA GCCTTCGTCA CTGGTCCCGC CACCAAACGT TTCGGCGAGA       2921

AGCAGGCCAT TATCGCCGGC ATGGCGGCCG ACGCGCTGGG CTACGTCTTG       2971

CTGGCGTTCG CGACGCGAGG CTGGATGGCC TTCCCCATTA TGATTCTTCT       3021

CGCTTCCGGC GGCATCGGGA TGCCCGCGTT GCAGGCCATG CTGTCCAGGC       3071
```

FIG. 7D

```
AGGTAGATGA CGACCATCAG GGACAGCTTC AAGGATCGCT CGCGGCTCTT   3121
ACCAGCCAGC AAAAGGCCAG GAACCGTAAA AAGGCCGCGT TGCTGGCGTT   3171
TTTCCATAGG CTCCGCCCCC CTGACGAGCA TCACAAAAAT CGACGCTCAA   3221
GTCAGAGGTG GCGAAACCCG ACAGGACTAT AAAGATACCA GGCGTTTCCC   3271
CCTGGAAGCT CCCTCGTGCG CTCTCCTGTT CCGACCCTGC CGCTTACCGG   3321
ATACCTGTCC GCCTTTCTCC CTTCGGGAAG CGTGGCGCTT TCTCAATGCT   3371
CACGCTGTAG GTATCTCAGT TCGGTGTAGG TCGTTCGCTC CAAGCTGGGC   3421
TGTGTGCACG AACCCCCCGT TCAGCCCGAC CGCTGCGCCT TATCCGGTAA   3471
CTATCGTCTT GAGTCCAACC CGGTAAGACA CGACTTATCG CCACTGGCAG   3521
CAGCCACTGG TAACAGGATT AGCAGAGCGA GGTATGTAGG CGGTGCTACA   3571
GAGTTCTTGA AGTGGTGGCC TAACTACGGC TACACTAGAA GGACAGTATT   3621
TGGTATCTGC GCTCTGCTGA AGCCAGTTAC CTTCGGAAAA AGAGTTGGTA   3671
GCTCTTGATC CGGCAAACAA ACCACCGCTG GTAGCGGTGG TTTTTTTGTT   3721
TGCAAGCAGC AGATTACGCG CAGAAAAAAA GGATCTCAAG AAGATCCTTT   3771
GATCTTTTCT ACGGGGTCTG ACGCTCAGTG GAACGAAAAC TCACGTTAAG   3821
GGATTTTGGT CATGAGATTA TCAAAAGGA TCTTCACCTA GATCCTTTTA    3871
AATTAAAAAT GAAGTTTTAA ATCAATCTAA AGTATATATG AGTAAACTTG   3921
GTCTGACAGT TACCAATGCT TAATCAGTGA GGCACCTATC TCAGCGATCT   3971
GTCTATTTCG TTCATCCATA GTTGCCTGAC TCCCCGTCGT GTAGATAACT   4021
ACGATACGGG AGGGCTTACC ATCTGGCCCC AGTGCTGCAA TGATACCGCG   4071
AGACCCACGC TCACCGGCTC CAGATTTATC AGCAATAAAC CAGCCAGCCG   4121
GAAGGGCCGA GCGCAGAAGT GGTCCTGCAA CTTTATCCGC CTCCATCCAG   4171
TCTATTAATT GTTGCCGGGA AGCTAGAGTA AGTAGTTCGC CAGTTAATAG   4221
TTTGCGCAAC GTTGTTGCCA TTGCTGCAGG CATCGTGGTG TCACGCTCGT   4271
CGTTTGGTAT GGCTTCATTC AGCTCCGGTT CCCAACGATC AAGGCGAGTT   4321
ACATGATCCC CCATGTTGTG CAAAAAAGCG GTTAGCTCCT TCGGTCCTCC   4371
```

FIG. 7E

```
GATCGTTGTC AGAAGTAAGT TGGCCGCAGT GTTATCACTC ATGGTTATGG    4421
CAGCACTGCA TAATTCTCTT ACTGTCATGC CATCCGTAAG ATGCTTTTCT    4471
GTGACTGGTG AGTACTCAAC CAAGTCATTC TGAGAATAGT GTATGCGGCG    4521
ACCGAGTTGC TCTTGCCCGG CGTCAACACG GGATAATACC GCGCCACATA    4571
GCAGAACTTT AAAAGTGCTC ATCATTGGAA AACGTTCTTC GGGGCGAAAA    4621
CTCTCAAGGA TCTTACCGCT GTTGAGATCC AGTTCGATGT AACCCACTCG    4671
TGCACCCAAC TGATCTTCAG CATCTTTTAC TTTCACCAGC GTTTCTGGGT    4721
GAGCAAAAAC AGGAAGGCAA AATGCCGCAA AAAGGGAAT AAGGGCGACA     4771
CGGAAATGTT GAATACTCAT ACTCTTCCTT TTTCAATATT ATTGAAGCAT    4821
TTATCAGGGT TATTGTCTCA TGAGCGGATA CATATTTGAA TGTATTTAGA    4871
AAAATAAACA ATAGGGGTT CCGCGCACAT TTCCCCGAAA AGTGCCACCT     4921
GACGTCTAAG AAACCATTAT TATCATGACA TTAACCTATA AAAATAGGCG    4971
TATCACGAGG CCCTTTCGT                                      4990
```

FIG. 7F

COSFclink  [SEQ ID NO: 3]

| | | | | |
|---|---|---|---|---|
| GACGTCGACG | GATCGGGAGA | TCGGGGATCG | ATCCGTCGAC | GTACGACTAG | 50 |
| TTATTAATAG | TAATCAATTA | CGGGGTCATT | AGTTCATAGC | CCATATATGG | 100 |
| AGTTCCGCGT | TACATAACTT | ACGGTAAATG | CCCGCCTGG | CTGACCGCCC | 150 |
| AACGACCCCC | GCCCATTGAC | GTCAATAATG | ACGTATGTTC | CCATAGTAAC | 200 |
| GCCAATAGGG | ACTTTCCATT | GACGTCAATG | GGTGGACTAT | TTACGGTAAA | 250 |
| CTGCCCACTT | GGCAGTACAT | CAAGTGTATC | ATATGCCAAG | TACGCCCCCT | 300 |
| ATTGACGTCA | ATGACGGTAA | ATGGCCCGCC | TGGCATTATG | CCCAGTACAT | 350 |
| GACCTTATGG | GACTTTCCTA | CTTGGCAGTA | CATCTACGTA | TTAGTCATCG | 400 |
| CTATTACCAT | GGTGATGCGG | TTTTGGCAGT | ACATCAATGG | GCGTGGATAG | 450 |
| CGGTTTGACT | CACGGGGATT | TCCAAGTCTC | CACCCCATTG | ACGTCAATGG | 500 |
| GAGTTTGTTT | TGGCACCAAA | ATCAACGGGA | CTTTCCAAAA | TGTCGTAACA | 550 |
| ACTCCGCCCC | ATTGACGCAA | ATGGGCGGTA | GGCGTGTACG | GTGGGAGGTC | 600 |
| TATATAAGCA | GAGCTGGGTA | CGTGAACCGT | CAGATCGCCT | GGAGACGCCA | 650 |
| TCGAATTCGG | TTACCTGCAG | ATATCAAGCT | AATTCGGTAC | CGAGCCCAAA | 700 |
| TCGGCCGACA | AAACTCACAC | ATGCCCACCG | TGCCCAGCAC | CTGAACTCCT | 750 |
| GGGGGGACCG | TCAGTCTTCC | TCTTCCCCCC | AAAACCCAAG | GACACCCTCA | 800 |
| TGATCTCCCG | GACCCCTGAG | GTCACATGCG | TGGTGGTGGA | CGTGAGCCAC | 850 |
| GAAGACCCTG | AGGTCAAGTT | CAACTGGTAC | GTGGACGGCG | TGGAGGTGCA | 900 |
| TAATGCCAAG | ACAAAGCCGC | GGGAGGAGCA | GTACAACAGC | ACGTACCGGG | 950 |
| TGGTCAGCGT | CCTCACCGTC | CTGCACCAGG | ACTGGCTGAA | TGGCAAGGAG | 1000 |
| TACAAGTGCA | AGGTCTCCAA | CAAAGCCCTC | CCAGCCCCA | TCGAGAAAAC | 1050 |
| CATCTCCAAA | GCCAAAGGGC | AGCCCCGAGA | ACCACAGGTG | TACACCCTGC | 1100 |
| CCCCATCCCG | GGATGAGCTG | ACCAAGAACC | AGGTCAGCCT | GACCTGCCTG | 1150 |
| GTCAAAGGCT | TCTATCCCAG | CGACATCGCC | GTGGAGTGGG | AGAGCAATGG | 1200 |
| GCAGCCGGAG | AACAACTACA | AGACCACGCC | TCCCGTGCTG | GACTCCGACG | 1250 |

FIG. 8A

```
GCTCCTTCTT CCTCTACAGC AAGCTCACCG TGGACAAGAG CAGGTGGCAG    1300
CAGGGGAACG TCTTCTCATG CTCCGTGATG CATGAGGCTC TGCACAACCA    1350
CTACACGCAG AAGAGCCTCT CCCTGTCTCC GGGTAAATGA GTGTAGTCTA    1400
GAGCTCGCTG ATCAGCCTCG ACTGTGCCTT CTAGTTGCCA GCCATCTGTT    1450
GTTTGCCCCT CCCCCGTGCC TTCCTTGACC CTGGAAGGTG CCACTCCCAC    1500
TGTCCTTTCC TAATAAAATG AGGAAATTGC ATCGCATTGT CTGAGTAGGT    1550
GTCATTCTAT TCTGGGGGGT GGGGTGGGGC AGGACAGCAA GGGGGAGGAT    1600
TGGGAAGACA ATAGCAGGCA TGCTGGGGAT GCGGTGGGCT CTATGGAACC    1650
AGCTGGGGCT CGAGGGGGGA TCTCCCGATC CCCAGCTTTG CTTCTCAATT    1700
TCTTATTTGC ATAATGAGAA AAAAAGGAAA ATTAATTTTA ACACCAATTC    1750
AGTAGTTGAT TGAGCAAATG CGTTGCCAAA AAGGATGCTT TAGAGACAGT    1800
GTTCTCTGCA CAGATAAGGA CAAACATTAT TCAGAGGGAG TACCCAGAGC    1850
TGAGACTCCT AAGCCAGTGA GTGGCACAGC ATTCTAGGGA GAAATATGCT    1900
TGTCATCACC GAAGCCTGAT TCCGTAGAGC CACACCTTGG TAAGGGCCAA    1950
TCTGCTCACA CAGGATAGAG AGGGCAGGAG CCAGGGCAGA GCATATAAGG    2000
TGAGGTAGGA TCAGTTGCTC CTCACATTTG CTTCTGACAT AGTTGTGTTG    2050
GGAGCTTGGA TAGCTTGGAC AGCTCAGGGC TGCGATTTCG CGCCAAACTT    2100
GACGGCAATC CTAGCGTGAA GGCTGGTAGG ATTTTATCCC CGCTGCCATC    2150
ATGGTTCGAC CATTGAACTG CATCGTCGCC GTGTCCCAAA ATATGGGGAT    2200
TGGCAAGAAC GGAGACCTAC CCTGGCCTCC GCTCAGGAAC GAGTTCAAGT    2250
ACTTCCAAAG AATGACCACA ACCTCTTCAG TGGAAGGTAA ACAGAATCTG    2300
GTGATTATGG GTAGGAAAAC CTGGTTCTCC ATTCCTGAGA AGAATCGACC    2350
TTTAAAGGAC AGAATTAATA TAGTTCTCAG TAGAGAACTC AAAGAACCAC    2400
CACGAGGAGC TCATTTTCTT GCCAAAAGTT TGGATGATGC CTTAAGACTT    2450
ATTGAACAAC CGGAATTGGC AAGTAAAGTA GACATGGTTT GGATAGTCGG    2500
AGGCAGTTCT GTTTACCAGG AAGCCATGAA TCAACCAGGC CACCTTAGAC    2550
```

FIG. 8B

```
TCTTTGTGAC AAGGATCATG CAGGAATTTG AAAGTGACAC GTTTTTCCCA    2600
GAAATTGATT TGGGGAAATA TAAACTTCTC CCAGAATACC CAGGCGTCCT    2650
CTCTGAGGTC CAGGAGGAAA AAGGCATCAA GTATAAGTTT GAAGTCTACG    2700
AGAAGAAAGA CTAACAGGAA GATGCTTTCA AGTTCTCTGC TCCCCTCCTA    2750
AAGCTATGCA TTTTTATAAG ACCATGCTAG CTTGAACTTG TTTATTGCAG    2800
CTTATAATGG TTACAAATAA AGCAATAGCA TCACAAATTT CACAAATAAA    2850
GCATTTTTT CACTGCATTC TAGTTGTGGT TTGTCCAAAC TCATCAATGT     2900
ATCTTATCAT GTCTGGATCA ACGATAGCTT ATCTGTGGGC GATGCCAAGC    2950
ACCTGGATGC TGTTGGTTTC CTGCTACTGA TTTAGAAGCC ATTTGCCCCC    3000
TGAGTGGGGC TTGGGAGCAC TAACTTTCTC TTTCAAAGGA AGCAATGCAG    3050
AAAGAAAAGC ATACAAAGTA TAAGCTGCCA TGTAATAATG AAGAAGATA     3100
AGGTTGTATG AATTAGATTT ACATACTTCT GAATTGAAAC TAAACACCTT    3150
TAAATTCTTA AATATATAAC ACATTTCATA TGAAAGTATT TTACATAAGT    3200
AACTCAGATA CATAGAAAAC AAAGCTAATG ATAGGTGTCC CTAAAAGTTC    3250
ATTTATTAAT TCTACAAATG ATGAGCTGGC CATCAAAATT CCAGCTCAAT    3300
TCTTCAACGA ATTAGAAAGA GCAATCTGCA AACTCATCTG GAATAACAAA    3350
AAACCTAGGA TAGCAAAAAC TCTTCTCAAG GATAAAAGAA CCTCTGGTGG    3400
AATCACCATG CCTGACCTAA AGCTGTACTA CAGAGCAATT GTGATAAAAA    3450
CTGCATGGTA CTGATATAGA AACGGACAAG TAGACCAATG GAATAGAACC    3500
CACACACCTA TGGTCACTTG ATCTTCAACA AGAGAGCTAA AACCATCCAC    3550
TGGAAAAAAG ACAGCATTTT CAACAAATGG TGCTGGCACA ACTGGTGGTT    3600
ATCATGGAGA AGAATGTGAA TTGATCCATT CCAATCTCCT TGTACTAAGG    3650
TCAAATCTAA GTGGATCAAG GAACTCCACA TAAAACCAGA GACACTGAAA    3700
CTTATAGAGG AGAAAGTGGG GAAAAGCCTC GAAGATATGG GCACAGGGGA    3750
AAAATTCCTG AATAGAACAG CAATGGCTTG TGCTGTAAGA TCGAGAATTG    3800
ACAAATGGGA CCTCATGAAA CTCCAAAGCT ATCGGATCAA TTCCTCCAAA    3850
```

FIG. 8C

```
AAAGCCTCCT CACTACTTCT GGAATAGCTC AGAGGCCGAG GCGGCCTCGG    3900
CCTCTGCATA AATAAAAAAA ATTAGTCAGC CATGCATGGG GCGGAGAATG    3950
GGCGGAACTG GGCGGAGTTA GGGGCGGGAT GGGCGGAGTT AGGGGCGGGA    4000
CTATGGTTGC TGACTAATTG AGATGCATGC TTTGCATACT TCTGCCTGCT    4050
GGGGAGCCTG GGGACTTTCC ACACCTGGTT GCTGACTAAT TGAGATGCAT    4100
GCTTTGCATA CTTCTGCCTG CTGGGGAGCC TGGGGACTTT CCACACCCTA    4150
ACTGACACAC ATTCCACAGA ATTAATTCCC GATCCCGTCG ACCTCGAGAG    4200
CTTGGCGTAA TCATGGTCAT AGCTGTTTCC TGTGTGAAAT TGTTATCCGC    4250
TCACAATTCC ACACAACATA CGAGCCGGAA GCATAAAGTG TAAAGCCTGG    4300
GGTGCCTAAT GAGTGAGCTA ACTCACATTA ATTGCGTTGC GCTCACTGCC    4350
CGCTTTCCAG TCGGGAAACC TGTCGTGCCA GCTGCATTAA TGAATCGGCC    4400
AACGCGCGGG GAGAGGCGGT TTGCGTATTG GCGCTCTTC CGCTTCCTCG    4450
CTCACTGACT CGCTGCGCTC GGTCGTTCGG CTGCGGCGAG CGGTATCAGC    4500
TCACTCAAAG GCGGTAATAC GGTTATCCAC AGAATCAGGG GATAACGCAG    4550
GAAAGAACAT GTGAGCAAAA GGCCAGCAAA AGGCCAGGAA CCGTAAAAAG    4600
GCCGCGTTGC TGGCGTTTTT CCATAGGCTC CGCCCCCCTG ACGAGCATCA    4650
CAAAAATCGA CGCTCAAGTC AGAGGTGGCG AAACCCGACA GGACTATAAA    4700
GATACCAGGC GTTTCCCCCT GGAAGCTCCC TCGTGCGCTC TCCTGTTCCG    4750
ACCCTGCCGC TTACCGGATA CCTGTCCGCC TTTCTCCCTT CGGGAAGCGT    4800
GGCGCTTTCT CAATGCTCAC GCTGTAGGTA TCTCAGTTCG GTGTAGGTCG    4850
TTCGCTCCAA GCTGGGCTGT GTGCACGAAC CCCCCGTTCA GCCCGACCGC    4900
TGCGCCTTAT CCGGTAACTA TCGTCTTGAG TCCAACCCGG TAAGACACGA    4950
CTTATCGCCA CTGGCAGCAG CCACTGGTAA CAGGATTAGC AGAGCGAGGT    5000
ATGTAGGCGG TGCTACAGAG TTCTTGAAGT GGTGGCCTAA CTACGGCTAC    5050
ACTAGAAGGA CAGTATTTGG TATCTGCGCT CTGCTGAAGC CAGTTACCTT    5100
```

FIG. 8D

| | | | | |
|---|---|---|---|---|
| CGGAAAAAGA | GTTGGTAGCT | CTTGATCCGG | CAAACAAACC | ACCGCTGGTA | 5150
| GCGGTGGTTT | TTTTGTTTGC | AAGCAGCAGA | TTACGCGCAG | AAAAAAGGA | 5200
| TCTCAAGAAG | ATCCTTTGAT | CTTTTCTACG | GGGTCTGACG | CTCAGTGGAA | 5250
| CGAAAACTCA | CGTTAAGGGA | TTTTGGTCAT | GAGATTATCA | AAAAGGATCT | 5300
| TCACCTAGAT | CCTTTTAAAT | TAAAAATGAA | GTTTTAAATC | AATCTAAAGT | 5350
| ATATATGAGT | AAACTTGGTC | TGACAGTTAC | CAATGCTTAA | TCAGTGAGGC | 5400
| ACCTATCTCA | GCGATCTGTC | TATTTCGTTC | ATCCATAGTT | GCCTGACTCC | 5450
| CCGTCGTGTA | GATAACTACG | ATACGGGAGG | GCTTACCATC | TGGCCCCAGT | 5500
| GCTGCAATGA | TACCGCGAGA | CCCACGCTCA | CCGGCTCCAG | ATTTATCAGC | 5550
| AATAAACCAG | CCAGCCGGAA | GGGCCGAGCG | CAGAAGTGGT | CCTGCAACTT | 5600
| TATCCGCCTC | CATCCAGTCT | ATTAATTGTT | GCCGGGAAGC | TAGAGTAAGT | 5650
| AGTTCGCCAG | TTAATAGTTT | GCGCAACGTT | GTTGCCATTG | CTACAGGCAT | 5700
| CGTGGTGTCA | CGCTCGTCGT | TTGGTATGGC | TTCATTCAGC | TCCGGTTCCC | 5750
| AACGATCAAG | GCGAGTTACA | TGATCCCCCA | TGTTGTGCAA | AAAAGCGGTT | 5800
| AGCTCCTTCG | GTCCTCCGAT | CGTTGTCAGA | AGTAAGTTGG | CCGCAGTGTT | 5850
| ATCACTCATG | GTTATGGCAG | CACTGCATAA | TTCTCTTACT | GTCATGCCAT | 5900
| CCGTAAGATG | CTTTTCTGTG | ACTGGTGAGT | ACTCAACCAA | GTCATTCTGA | 5950
| GAATAGTGTA | TGCGGCGACC | GAGTTGCTCT | TGCCCGGCGT | CAATACGGGA | 6000
| TAATACCGCG | CCACATAGCA | GAACTTTAAA | AGTGCTCATC | ATTGGAAAAC | 6050
| GTTCTTCGGG | GCGAAAACTC | TCAAGGATCT | TACCGCTGTT | GAGATCCAGT | 6100
| TCGATGTAAC | CCACTCGTGC | ACCCAACTGA | TCTTCAGCAT | CTTTTACTTT | 6150
| CACCAGCGTT | TCTGGGTGAG | CAAAAACAGG | AAGGCAAAAT | GCCGCAAAAA | 6200
| AGGGAATAAG | GGCGACACGG | AAATGTTGAA | TACTCATACT | CTTCCTTTTT | 6250
| CAATATTATT | GAAGCATTTA | TCAGGGTTAT | TGTCTCATGA | GCGGATACAT | 6300
| ATTTGAATGT | ATTTAGAAAA | ATAAACAAAT | AGGGGTTCCG | CGCACATTTC | 6350
| CCCGAAAAGT | GCCACCT | | | 6367

FIG. 8E

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 4990 base pairs
      (B) TYPE: nucleic acid
      (C) STRANDEDNESS: double
      (D) TOPOLOGY: Not Relevant (ii) MOLECULE TYPE: cDNA (ix) FEATURE:
    (A) NAME/KEY: CDS
    (B) LOCATION: 898..2361

(xi) SEQUENCE DESCRIPTION: SEQ ID NO: 1:

```
TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGGCTGG CTTAACTATG CGGCATCAGA GCAGATTGTA CTGAGAGTGC     180

ACCATATGCG GTGTGAAATA CCGCACAGAT GCGTAAGGAG AAAATACCGC ATCAGGCGCC     240

ATTCGCCATT CAGGCTGCGC AACTGTTGGG AAGGGCGATC GGTGCGGGCC TCTTCGCTAT     300

TACGCCAGCT GGCGAAAGGG GGATGTGCTG CAAGGCGATT AAGTTGGGTA ACGCCAGGGT     360

TTTCCCAGTC ACGACGTTGT AAAACGACGG CCAGTGCCAG TGAATTCGTT GCAGGACAGG     420

ATGTGGTGCC CGATGTGACT AGCTCTTTGC TGCAGGCCGT CCTATCCTCT GGTTCCGATA     480

AGAGACCCAG AACTCCGGCC CCCACCGCC CACCGCCACC CCCATACATA TGTGGTACGC      540

AAGTAAGAGT GCCTGCGCAT GCCCCATGTG CCCCACCAAG AGTTTTGCAT CCCATACAAG     600

TCCCCAAAGT GGAGAACCGA ACCAATTCTT CGCGGGCAGA ACAAAAGCTT CTGCACACGT     660

CTCCACTCGA ATTTGGAGCC GGCCGGCGTG TGCAAAAGAG GTGAATCGAA CGAAAGACCC     720

GTGTGTAAAG CCGCGTTTCC AAAATGTATA AAACCGAGAG CATCTGGCCA ATGTGCATCA     780

GTTGTGGTCA GCAGCAAAAT CAAGTGAATC ATCTCAGTGC AACTAAAGGG GGGATCCGAT     840

ATCCAAGGTT ACCGCGGACT AGTCTAGTAA CGGCCGCCAG TGTGCTGGAA TTCGGCT       897
```

| | | | |
|---|---|---|---|
| ATG GAC CAC CTC GGG GCG TCC CTC TGG CCC CAG GTC GGC TCC CTT TGT | | | 945 |
| Met Asp His Leu Gly Ala Ser Leu Trp Pro Gln Val Gly Ser Leu Cys | | | |
| 1               5                   10                  15 | | | |
| CTC CTG CTC GCT GGG GCC GCC TGG GCG CCC CCG CCT AAC CTC CCG GAC | | | 993 |
| Leu Leu Leu Ala Gly Ala Ala Trp Ala Pro Pro Pro Asn Leu Pro Asp | | | |
|             20                  25                  30 | | | |
| CCC AAG TTC GAG AGC AAA GCG GCC TTG CTG GCG GCC CGG GGG CCC GAA | | | 1041 |
| Pro Lys Phe Glu Ser Lys Ala Ala Leu Leu Ala Ala Arg Gly Pro Glu | | | |
|         35                  40                  45 | | | |
| GAG CTT CTG TGC TTC ACC GAG CGG TTG GAG GAC TTG GTG TGT TTC TGG | | | 1089 |
| Glu Leu Leu Cys Phe Thr Glu Arg Leu Glu Asp Leu Val Cys Phe Trp | | | |
|     50                  55                  60 | | | |
| GAG GAA GCG GCG AGC GCT GGG GTG GGC CCG GGC AAC TAC AGC TTC TCC | | | 1137 |
| Glu Glu Ala Ala Ser Ala Gly Val Gly Pro Gly Asn Tyr Ser Phe Ser | | | |
| 65                  70                  75                  80 | | | |
| TAC CAG CTC GAG GAT GAG CCA TGG AAG CTG TGT CGC CTG CAC CAG GCT | | | 1185 |
| Tyr Gln Leu Glu Asp Glu Pro Trp Lys Leu Cys Arg Leu His Gln Ala | | | |
|                 85                  90                  95 | | | |
| CCC ACG GCT CGT GGT GCG GTG CGC TTC TGG TGT TCG CTG CCT ACA GCC | | | 1233 |
| Pro Thr Ala Arg Gly Ala Val Arg Phe Trp Cys Ser Leu Pro Thr Ala | | | |
|             100                 105                 110 | | | |
| GAC ACG TCG AGC TTC GTG CCC CTA GAG TTG CGC GTC ACA GCA GCC TCC | | | 1281 |
| Asp Thr Ser Ser Phe Val Pro Leu Glu Leu Arg Val Thr Ala Ala Ser | | | |
|         115                 120                 125 | | | |
| GGC GCT CCG CGA TAT CAC CGT GTC ATC CAC ATC AAT GAA GTA GTG CTC | | | 1329 |
| Gly Ala Pro Arg Tyr His Arg Val Ile His Ile Asn Glu Val Val Leu | | | |
|     130                 135                 140 | | | |
| CTA GAC GCC CCC GTG GGG CTG GTG GCG CGG TTG GCT GAC GAG AGC GGC | | | 1377 |
| Leu Asp Ala Pro Val Gly Leu Val Ala Arg Leu Ala Asp Glu Ser Gly | | | |
| 145                 150                 155                 160 | | | |

```
CAC GTA GTG TTG CGC TGG CTC CCG CCG CCT GAG ACA CCC ATG ACG TCT     1425
His Val Val Leu Arg Trp Leu Pro Pro Pro Glu Thr Pro Met Thr Ser
            165                 170                 175

CAC ATC CGC TAC GAG GTG GAC GTC TCG GCC GGC AAC GGC GCA GGG AGC     1473
His Ile Arg Tyr Glu Val Asp Val Ser Ala Gly Asn Gly Ala Gly Ser
        180                 185                 190

GTA CAG AGG GTG GAG ATC CTG GAG GGC CGC ACC GAG TGT GTG CTG AGC     1521
Val Gln Arg Val Glu Ile Leu Glu Gly Arg Thr Glu Cys Val Leu Ser
    195                 200                 205

AAC CTG CGG GGC CGG ACG CGC TAC ACC TTC GCC GTC CGC GCG CGT ATG     1569
Asn Leu Arg Gly Arg Thr Arg Tyr Thr Phe Ala Val Arg Ala Arg Met
210                 215                 220

GCT GAG CCG AGC TTC GGC GGC TTC TGG AGC GCC TGG TCG GAG CCT GTG     1617
Ala Glu Pro Ser Phe Gly Gly Phe Trp Ser Ala Trp Ser Glu Pro Val
225                 230                 235                 240

TCG CTG CTG ACG CCT AGC GAC CTG GAC CCC ATT GAG GGC CGT GGT ACC     1665
Ser Leu Leu Thr Pro Ser Asp Leu Asp Pro Ile Glu Gly Arg Gly Thr
        245                 250                 255

GAG CCC AAA TCG GCC GAC AAA ACT CAC ACA TGC CCA CCG TGC CCA GCA     1713
Glu Pro Lys Ser Ala Asp Lys Thr His Thr Cys Pro Pro Cys Pro Ala
            260                 265                 270

CCT GAA CTC CTG GGG GGA CCG TCA GTC TTC CTC TTC CCC CCA AAA CCC     1761
Pro Glu Leu Leu Gly Gly Pro Ser Val Phe Leu Phe Pro Pro Lys Pro
                275                 280                 285

AAG GAC ACC CTC ATG ATC TCC CGG ACC CCT GAG GTC ACA TGC GTG GTG     1809
Lys Asp Thr Leu Met Ile Ser Arg Thr Pro Glu Val Thr Cys Val Val
290                 295                 300

GTG GAC GTG AGC CAC GAA GAC CCT GAG GTC AAG TTC AAC TGG TAC GTG     1857
Val Asp Val Ser His Glu Asp Pro Glu Val Lys Phe Asn Trp Tyr Val
305                 310                 315                 320

GAC GGC GTG GAG GTG CAT AAT GCC AAG ACA AAG CCG CGG GAG GAG CAG     1905
Asp Gly Val Glu Val His Asn Ala Lys Thr Lys Pro Arg Glu Glu Gln
        325                 330                 335

TAC AAC AGC ACG TAC CGG GTG GTC AGC GTC CTC ACC GTC CTG CAC CAG     1953
Tyr Asn Ser Thr Tyr Arg Val Val Ser Val Leu Thr Val Leu His Gln
    340                 345                 350

GAC TGG CTG AAT GGC AAG GAG TAC AAG TGC AAG GTC TCC AAC AAA GCC     2001
Asp Trp Leu Asn Gly Lys Glu Tyr Lys Cys Lys Val Ser Asn Lys Ala
355                 360                 365

CTC CCA GCC CCC ATC GAG AAA ACC ATC TCC AAA GCC AAA GGG CAG CCC     2049
Leu Pro Ala Pro Ile Glu Lys Thr Ile Ser Lys Ala Lys Gly Gln Pro
370                 375                 380

CGA GAA CCA CAG GTG TAC ACC CTG CCC CCA TCC CGG GAT GAG CTG ACC     2097
Arg Glu Pro Gln Val Tyr Thr Leu Pro Pro Ser Arg Asp Glu Leu Thr
385                 390                 395                 400

AAG AAC CAG GTC AGC CTG ACC TGC CTG GTC AAA GGC TTC TAT CCC AGC     2145
Lys Asn Gln Val Ser Leu Thr Cys Leu Val Lys Gly Phe Tyr Pro Ser
            405                 410                 415

GAC ATC GCC GTG GAG TGG GAG AGC AAT GGG CAG CCG GAG AAC AAC TAC     2193
Asp Ile Ala Val Glu Trp Glu Ser Asn Gly Gln Pro Glu Asn Asn Tyr
        420                 425                 430

AAG ACC ACG CCT CCC GTG CTG GAC TCC GAC GGC TCC TTC TTC CTC TAC     2241
Lys Thr Thr Pro Pro Val Leu Asp Ser Asp Gly Ser Phe Phe Leu Tyr
    435                 440                 445

AGC AAG CTC ACC GTG GAC AAG AGC AGG TGG CAG CAG GGG AAC GTC TTC     2289
Ser Lys Leu Thr Val Asp Lys Ser Arg Trp Gln Gln Gly Asn Val Phe
450                 455                 460

TCA TGC TCC GTG ATG CAT GAG GCT CTG CAC AAC CAC TAC ACG CAG AAG     2337
Ser Cys Ser Val Met His Glu Ala Leu His Asn His Tyr Thr Gln Lys
465                 470                 475                 480
```

```
AGC CTC TCC CTG TCT CCG GGT AAA TGAGTGTAGT CTAGAAGCTT ACGCGTAGGC    2391
Ser Leu Ser Leu Ser Pro Gly Lys
              485

CTGAGCTCGC TGATCAGCCT CGAGGATCCA GACATGATAA GATACATTGA TGAGTTTGGA    2451

CAAACCACAA CTAGAATGCA GTGAAAAAAA TGCTTTATTT GTGAAATTTG TGATGCTATT    2511

GCTTTATTTG TAACCATTAT AAGCTGCAAT AAACAAGTTA ACAACAACAA TTGCATTCAT    2571

TTTATGTTTC AGGTTCAGGG GGAGGTGTGG GAGGTTTTTT AAAGCAAGTA AAACCTCTAC    2631

AAATGTGGTA TGGCTGATTA TGATCAGTCG ACCGATGCCC TTGAGAGCCT TCAACCCAGT    2691

CAGCTCCTTC CGGTGGGCGC GGGGCATGAC TATCGTCGCC GCACTTATGA CTGTCTTCTT    2751

TATCATGCAA CTCGTAGGAC AGGTGCCGGC AGCGCTCTGG GTCATTTTCG GCGAGGACCG    2811

CTTTCGCTGG AGCGCGACGA TGATCGGCCT GTCGCTTGCG GTATTCGGAA TCTTGCACGC    2871

CCTCGCTCAA GCCTTCGTCA CTGGTCCCGC CACCAAACGT TTCGGCGAGA AGCAGGCCAT    2931

TATCGCCGGC ATGGCGGCCG ACGCGCTGGG CTACGTCTTG CTGGCGTTCG CGACGCGAGG    2991

CTGGATGGCC TTCCCCATTA TGATTCTTCT CGCTTCCGGC GGCATCGGGA TGCCCGCGTT    3051

GCAGGCCATG CTGTCCAGGC AGGTAGATGA CGACCATCAG GGACAGCTTC AAGGATCGCT    3111

CGCGGCTCTT ACCAGCCAGC AAAAGGCCAG GAACCGTAAA AAGGCCGCGT TGCTGGCGTT    3171

TTTCCATAGG CTCCGCCCCC CTGACGAGCA TCACAAAAAT CGACGCTCAA GTCAGAGGTG    3231

GCGAAACCCG ACAGGACTAT AAAGATACCA GGCGTTTCCC CCTGGAAGCT CCCTCGTGCG    3291

CTCTCCTGTT CCGACCCTGC CGCTTACCGG ATACCTGTCC GCCTTTCTCC CTTCGGGAAG    3351

CGTGGCGCTT TCTCAATGCT CACGCTGTAG GTATCTCAGT TCGGTGTAGG TCGTTCGCTC    3411

CAAGCTGGGC TGTGTGCACG AACCCCCCGT TCAGCCCGAC CGCTGCGCCT TATCCGGTAA    3471

CTATCGTCTT GAGTCCAACC CGGTAAGACA CGACTTATCG CCACTGGCAG CAGCCACTGG    3531

TAACAGGATT AGCAGAGCGA GGTATGTAGG CGGTGCTACA GAGTTCTTGA AGTGGTGGCC    3591

TAACTACGGC TACACTAGAA GGACAGTATT TGGTATCTGC GCTCTGCTGA AGCCAGTTAC    3651

CTTCGGAAAA AGAGTTGGTA GCTCTTGATC CGGCAAACAA ACCACCGCTG GTAGCGGTGG    3711

TTTTTTTGTT TGCAAGCAGC AGATTACGCG CAGAAAAAAA GGATCTCAAG AAGATCCTTT    3771

GATCTTTTCT ACGGGGTCTG ACGCTCAGTG GAACGAAAAC TCACGTTAAG GGATTTTGGT    3831

CATGAGATTA TCAAAAAGGA TCTTCACCTA GATCCTTTTA AATTAAAAAT GAAGTTTTAA    3891

ATCAATCTAA AGTATATATG AGTAAACTTG GTCTGACAGT TACCAATGCT TAATCAGTGA    3951

GGCACCTATC TCAGCGATCT GTCTATTTCG TTCATCCATA GTTGCCTGAC TCCCCGTCGT    4011

GTAGATAACT ACGATACGGG AGGGCTTACC ATCTGGCCCC AGTGCTGCAA TGATACCGCG    4071

AGACCCACGC TCACCGGCTC CAGATTTATC AGCAATAAAC CAGCCAGCCG GAAGGGCCGA    4131

GCGCAGAAGT GGTCCTGCAA CTTTATCCGC CTCCATCCAG TCTATTAATT GTTGCCGGGA    4191

AGCTAGAGTA AGTAGTTCGC CAGTTAATAG TTTGCGCAAC GTTGTTGCCA TTGCTGCAGG    4251

CATCGTGGTG TCACGCTCGT CGTTTGGTAT GGCTTCATTC AGCTCCGGTT CCCAACGATC    4311

AAGGCGAGTT ACATGATCCC CCATGTTGTG CAAAAAAGCG GTTAGCTCCT TCGGTCCTCC    4371

GATCGTTGTC AGAAGTAAGT TGGCCGCAGT GTTATCACTC ATGGTTATGG CAGCACTGCA    4431

TAATTCTCTT ACTGTCATGC CATCCGTAAG ATGCTTTTCT GTGACTGGTG AGTACTCAAC    4491

CAAGTCATTC TGAGAATAGT GTATGCGGCG ACCGAGTTGC TCTTGCCCGG CGTCAACACG    4551

GGATAATACC GCGCCACATA GCAGAACTTT AAAAGTGCTC ATCATTGGAA AACGTTCTTC    4611
```

```
GGGGCGAAAA CTCTCAAGGA TCTTACCGCT GTTGAGATCC AGTTCGATGT AACCCACTCG    4671

TGCACCCAAC TGATCTTCAG CATCTTTTAC TTTCACCAGC GTTTCTGGGT GAGCAAAAAC    4731

AGGAAGGCAA AATGCCGCAA AAAGGGAAT AAGGGCGACA CGGAAATGTT GAATACTCAT     4791

ACTCTTCCTT TTTCAATATT ATTGAAGCAT TTATCAGGGT TATTGTCTCA TGAGCGGATA    4851

CATATTTGAA TGTATTTAGA AAATAAACA AATAGGGGTT CCGCGCACAT TTCCCCGAAA     4911

AGTGCCACCT GACGTCTAAG AAACCATTAT TATCATGACA TTAACCTATA AAAATAGGCG    4971

TATCACGAGG CCCTTTCGT                                                 4990

(2) INFORMATION FOR SEQ ID NO: 2:

(i) SEQUENCE CHARACTERISTICS:
        (A) LENGTH: 488 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp His Leu Gly Ala Ser Leu Trp Pro Gln Val Gly Ser Leu Cys
 1               5                  10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Ile Glu Gly Arg Gly Thr
                245                 250                 255

Glu Pro Lys Ser Ala Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285
```

```
Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

(2) INFORMATION FOR SEQ ID NO: 3:

(i) SEQUENCE CHARACTERISTICS:
         (A) LENGTH: 6367 base pairs
         (B) TYPE: nucleic acid
         (C) STRANDEDNESS: double
         (D) TOPOLOGY: Not Relevant (ii) MOLECULE TYPE: cDNA (xi) SEQUENCE DESCRIPTION: SEQ ID NO: 3:

GACGTCGACG GATCGGGAGA TCGGGGATCG ATCCGTCGAC GTACGACTAG TTATTAATAG      60

TAATCAATTA CGGGGTCATT AGTTCATAGC CCATATATGG AGTTCCGCGT TACATAACTT     120

ACGGTAAATG GCCCGCCTGG CTGACCGCCC AACGACCCCC GCCCATTGAC GTCAATAATG     180

ACGTATGTTC CCATAGTAAC GCCAATAGGG ACTTTCCATT GACGTCAATG GGTGGACTAT     240

TTACGGTAAA CTGCCCACTT GGCAGTACAT CAAGTGTATC ATATGCCAAG TACGCCCCCT     300

ATTGACGTCA ATGACGGTAA ATGGCCCGCC TGGCATTATG CCCAGTACAT GACCTTATGG     360

GACTTTCCTA CTTGGCAGTA CATCTACGTA TTAGTCATCG CTATTACCAT GGTGATGCGG     420

TTTTGGCAGT ACATCAATGG GCGTGGATAG CGGTTTGACT CACGGGGATT TCCAAGTCTC     480

CACCCCATTG ACGTCAATGG GAGTTTGTTT TGGCACCAAA ATCAACGGGA CTTTCCAAAA     540

TGTCGTAACA ACTCCGCCCC ATTGACGCAA ATGGGCGGTA GGCGTGTACG GTGGGAGGTC     600

TATATAAGCA GAGCTGGGTA CGTGAACCGT CAGATCGCCT GGAGACGCCA TCGAATTCGG     660

TTACCTGCAG ATATCAAGCT AATTCGGTAC CGAGCCCAAA TCGGCCGACA AAACTCACAC     720

ATGCCCACCG TGCCCAGCAC CTGAACTCCT GGGGGGACCG TCAGTCTTCC TCTTCCCCCC     780
```

```
                                    -continued

AAAACCCAAG GACACCCTCA TGATCTCCCG GACCCCTGAG GTCACATGCG TGGTGGTGGA    840

CGTGAGCCAC GAAGACCCTG AGGTCAAGTT CAACTGGTAC GTGGACGGCG TGGAGGTGCA    900

TAATGCCAAG ACAAAGCCGC GGGAGGAGCA GTACAACAGC ACGTACCGGG TGGTCAGCGT    960

CCTCACCGTC CTGCACCAGG ACTGGCTGAA TGGCAAGGAG TACAAGTGCA AGGTCTCCAA   1020

CAAAGCCCTC CCAGCCCCCA TCGAGAAAAC CATCTCCAAA GCCAAAGGGC AGCCCCGAGA   1080

ACCACAGGTG TACACCCTGC CCCCATCCCG GGATGAGCTG ACCAAGAACC AGGTCAGCCT   1140

GACCTGCCTG GTCAAAGGCT TCTATCCCAG CGACATCGCC GTGGAGTGGG AGAGCAATGG   1200

GCAGCCGGAG AACAACTACA AGACCACGCC TCCCGTGCTG GACTCCGACG GCTCCTTCTT   1260

CCTCTACAGC AAGCTCACCG TGGACAAGAG CAGGTGGCAG CAGGGGAACG TCTTCTCATG   1320

CTCCGTGATG CATGAGGCTC TGCACAACCA CTACACGCAG AAGAGCCTCT CCCTGTCTCC   1380

GGGTAAATGA GTGTAGTCTA GAGCTCGCTG ATCAGCCTCG ACTGTGCCTT CTAGTTGCCA   1440

GCCATCTGTT GTTTGCCCCT CCCCCGTGCC TTCCTTGACC CTGGAAGGTG CCACTCCCAC   1500

TGTCCTTTCC TAATAAAATG AGGAAATTGC ATCGCATTGT CTGAGTAGGT GTCATTCTAT   1560

TCTGGGGGGT GGGGTGGGGC AGGACAGCAA GGGGGAGGAT TGGGAAGACA ATAGCAGGCA   1620

TGCTGGGGAT GCGGTGGGCT CTATGGAACC AGCTGGGGCT CGAGGGGGGA TCTCCCGATC   1680

CCCAGCTTTG CTTCTCAATT TCTTATTTGC ATAATGAGAA AAAAAGGAAA ATTAATTTTA   1740

ACACCAATTC AGTAGTTGAT TGAGCAAATG CGTTGCCAAA AAGGATGCTT TAGAGACAGT   1800

GTTCTCTGCA CAGATAAGGA CAAACATTAT TCAGAGGGAG TACCCAGAGC TGAGACTCCT   1860

AAGCCAGTGA GTGGCACAGC ATTCTAGGGA GAAATATGCT TGTCATCACC GAAGCCTGAT   1920

TCCGTAGAGC CACACCTTGG TAAGGGCCAA TCTGCTCACA CAGGATAGAG AGGGCAGGAG   1980

CCAGGGCAGA GCATATAAGG TGAGGTAGGA TCAGTTGCTC CTCACATTTG CTTCTGACAT   2040

AGTTGTGTTG GGAGCTTGGA TAGCTTGGAC AGCTCAGGGC TGCGATTTCG CGCCAAACTT   2100

GACGGCAATC CTAGCGTGAA GGCTGGTAGG ATTTTATCCC CGCTGCCATC ATGGTTCGAC   2160

CATTGAACTG CATCGTCGCC GTGTCCCAAA ATATGGGGAT TGGCAAGAAC GGAGACCTAC   2220

CCTGGCCTCC GCTCAGGAAC GAGTTCAAGT ACTTCCAAAG AATGACCACA ACCTCTTCAG   2280

TGGAAGGTAA ACAGAATCTG GTGATTATGG GTAGGAAAAC CTGGTTCTCC ATTCCTGAGA   2340

AGAATCGACC TTTAAAGGAC AGAATTAATA TAGTTCTCAG TAGAGAACTC AAAGAACCAC   2400

CACGAGGAGC TCATTTTCTT GCCAAAAGTT TGGATGATGC CTTAAGACTT ATTGAACAAC   2460

CGGAATTGGC AAGTAAAGTA GACATGGTTT GGATAGTCGG AGGCAGTTCT GTTTACCAGG   2520

AAGCCATGAA TCAACCAGGC CACCTTAGAC TCTTTGTGAC AAGGATCATG CAGGAATTTG   2580

AAAGTGACAC GTTTTTCCCA GAAATTGATT TGGGGAAATA TAAACTTCTC CCAGAATACC   2640

CAGGCGTCCT CTCTGAGGTC CAGGAGGAAA AAGGCATCAA GTATAAGTTT GAAGTCTACG   2700

AGAAGAAAGA CTAACAGGAA GATGCTTTCA AGTTCTCTGC TCCCCTCCTA AAGCTATGCA   2760

TTTTTATAAG ACCATGCTAG CTTGAACTTG TTTATTGCAG CTTATAATGG TTACAAATAA   2820

AGCAATAGCA TCACAAATTT CACAAATAAA GCATTTTTTT CACTGCATTC TAGTTGTGGT   2880

TTGTCCAAAC TCATCAATGT ATCTTATCAT GTCTGGATCA ACGATAGCTT ATCTGTGGGC   2940

GATGCCAAGC ACCTGGATGC TGTTGGTTTC CTGCTACTGA TTTAGAAGCC ATTTGCCCCC   3000

TGAGTGGGGC TTGGGAGCAC TAACTTTCTC TTTCAAAGGA AGCAATGCAG AAAGAAAAGC   3060

ATACAAAGTA TAAGCTGCCA TGTAATAATG GAAGAAGATA AGGTTGTATG AATTAGATTT   3120

ACATACTTCT GAATTGAAAC TAAACACCTT TAAATTCTTA AATATATAAC ACATTTCATA   3180
```

-continued

```
TGAAAGTATT TTACATAAGT AACTCAGATA CATAGAAAAC AAAGCTAATG ATAGGTGTCC      3240

CTAAAAGTTC ATTTATTAAT TCTACAAATG ATGAGCTGGC CATCAAAATT CCAGCTCAAT      3300

TCTTCAACGA ATTAGAAAGA GCAATCTGCA AACTCATCTG GAATAACAAA AAACCTAGGA      3360

TAGCAAAAAC TCTTCTCAAG GATAAAAGAA CCTCTGGTGG AATCACCATG CCTGACCTAA      3420

AGCTGTACTA CAGAGCAATT GTGATAAAAA CTGCATGGTA CTGATATAGA AACGGACAAG      3480

TAGACCAATG GAATAGAACC CACACACCTA TGGTCACTTG ATCTTCAACA AGAGAGCTAA      3540

AACCATCCAC TGGAAAAAAG ACAGCATTTT CAACAAATGG TGCTGGCACA ACTGGTGGTT      3600

ATCATGGAGA AGAATGTGAA TTGATCCATT CCAATCTCCT TGTACTAAGG TCAAATCTAA      3660

GTGGATCAAG GAACTCCACA TAAAACCAGA GACACTGAAA CTTATAGAGG AGAAAGTGGG      3720

GAAAAGCCTC GAAGATATGG GCACAGGGGA AAAATTCCTG AATAGAACAG CAATGGCTTG      3780

TGCTGTAAGA TCGAGAATTG ACAAATGGGA CCTCATGAAA CTCCAAAGCT ATCGGATCAA      3840

TTCCTCCAAA AAAGCCTCCT CACTACTTCT GGAATAGCTC AGAGGCCGAG GCGGCCTCGG      3900

CCTCTGCATA ATAAAAAAAA ATTAGTCAGC CATGCATGGG GCGAGAATG GCGGAACTG       3960

GGCGGAGTTA GGGGCGGGAT GGGCGGAGTT AGGGGCGGGA CTATGGTTGC TGACTAATTG      4020

AGATGCATGC TTTGCATACT TCTGCCTGCT GGGGAGCCTG GGGACTTTCC ACACCTGGTT      4080

GCTGACTAAT TGAGATGCAT GCTTTGCATA CTTCTGCCTG CTGGGGAGCC TGGGGACTTT      4140

CCACACCCTA ACTGACACAC ATTCCACAGA ATTAATTCCC GATCCCGTCG ACCTCGAGAG      4200

CTTGGCGTAA TCATGGTCAT AGCTGTTTCC TGTGTGAAAT TGTTATCCGC TCACAATTCC      4260

ACACAACATA CGAGCCGGAA GCATAAAGTG TAAAGCCTGG GGTGCCTAAT GAGTGAGCTA      4320

ACTCACATTA ATTGCGTTGC GCTCACTGCC CGCTTTCCAG TCGGGAAACC TGTCGTGCCA      4380

GCTGCATTAA TGAATCGGCC AACGCGCGGG GAGAGGCGGT TTGCGTATTG GGCGCTCTTC      4440

CGCTTCCTCG CTCACTGACT CGCTGCGCTC GGTCGTTCGG CTGCGGCGAG CGGTATCAGC      4500

TCACTCAAAG GCGGTAATAC GGTTATCCAC AGAATCAGGG GATAACGCAG GAAAGAACAT      4560

GTGAGCAAAA GGCCAGCAAA AGGCCAGGAA CCGTAAAAAG GCCGCGTTGC TGGCGTTTTT      4620

CCATAGGCTC CGCCCCCCTG ACGAGCATCA CAAAAATCGA CGCTCAAGTC AGAGGTGGCG      4680

AAACCCGACA GGACTATAAA GATACCAGGC GTTTCCCCCT GGAAGCTCCC TCGTGCGCTC      4740

TCCTGTTCCG ACCCTGCCGC TTACCGGATA CCTGTCCGCC TTTCTCCCTT CGGGAAGCGT      4800

GGCGCTTTCT CAATGCTCAC GCTGTAGGTA TCTCAGTTCG GTGTAGGTCG TTCGCTCCAA      4860

GCTGGGCTGT GTGCACGAAC CCCCCGTTCA GCCCGACCGC TGCGCCTTAT CCGGTAACTA      4920

TCGTCTTGAG TCCAACCCGG TAAGACACGA CTTATCGCCA CTGGCAGCAG CCACTGGTAA      4980

CAGGATTAGC AGAGCGAGGT ATGTAGGCGG TGCTACAGAG TTCTTGAAGT GGTGGCCTAA      5040

CTACGGCTAC ACTAGAAGGA CAGTATTTGG TATCTGCGCT CTGCTGAAGC CAGTTACCTT      5100

CGGAAAAAGA GTTGGTAGCT CTTGATCCGG CAAACAAACC ACCGCTGGTA GCGGTGGTTT      5160

TTTTGTTTGC AAGCAGCAGA TTACGCGCAG AAAAAAAGGA TCTCAAGAAG ATCCTTTGAT      5220

CTTTTCTACG GGGTCTGACG CTCAGTGGAA CGAAAACTCA CGTTAAGGGA TTTTGGTCAT      5280

GAGATTATCA AAAAGGATCT TCACCTAGAT CCTTTTAAAT TAAAAATGAA GTTTTAAATC      5340

AATCTAAAGT ATATATGAGT AAACTTGGTC TGACAGTTAC CAATGCTTAA TCAGTGAGGC      5400

ACCTATCTCA GCGATCTGTC TATTTCGTTC ATCCATAGTT GCCTGACTCC CCGTCGTGTA      5460

GATAACTACG ATACGGGAGG GCTTACCATC TGGCCCCAGT GCTGCAATGA TACCGCGAGA      5520
```

```
CCCACGCTCA CCGGCTCCAG ATTTATCAGC AATAAACCAG CCAGCCGGAA GGGCCGAGCG      5580

CAGAAGTGGT CCTGCAACTT TATCCGCCTC CATCCAGTCT ATTAATTGTT GCCGGGAAGC      5640

TAGAGTAAGT AGTTCGCCAG TTAATAGTTT GCGCAACGTT GTTGCCATTG CTACAGGCAT      5700

CGTGGTGTCA CGCTCGTCGT TTGGTATGGC TTCATTCAGC TCCGGTTCCC AACGATCAAG      5760

GCGAGTTACA TGATCCCCCA TGTTGTGCAA AAAAGCGGTT AGCTCCTTCG GTCCTCCGAT      5820

CGTTGTCAGA AGTAAGTTGG CCGCAGTGTT ATCACTCATG GTTATGGCAG CACTGCATAA      5880

TTCTCTTACT GTCATGCCAT CCGTAAGATG CTTTTCTGTG ACTGGTGAGT ACTCAACCAA      5940

GTCATTCTGA GAATAGTGTA TGCGGCGACC GAGTTGCTCT TGCCCGGCGT CAATACGGGA      6000

TAATACCGCG CCACATAGCA GAACTTTAAA AGTGCTCATC ATTGGAAAAC GTTCTTCGGG      6060

GCGAAAACTC TCAAGGATCT TACCGCTGTT GAGATCCAGT TCGATGTAAC CCACTCGTGC      6120

ACCCAACTGA TCTTCAGCAT CTTTTACTTT CACCAGCGTT TCTGGGTGAG CAAAAACAGG      6180

AAGGCAAAAT GCCGCAAAAA AGGGAATAAG GGCGACACGG AAATGTTGAA TACTCATACT      6240

CTTCCTTTTT CAATATTATT GAAGCATTTA TCAGGGTTAT TGTCTCATGA GCGGATACAT      6300

ATTTGAATGT ATTTAGAAAA ATAAACAAAT AGGGGTTCCG CGCACATTTC CCCGAAAAGT      6360

GCCACCT                                                                6367

(2) INFORMATION FOR SEQ ID NO: 4:

(i) SEQUENCE CHARACTERISTICS:
        (A) LENGTH: 38 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 4:

GTATCATGGA CCACCTCGGG GCGTCCCTCT GGCCCCAG                              38

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 5:

ATGGACCACC TCGGGGCGTC CCTCTGGCCC CAG                                   33

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 6:

GTGTCCTAAG AGCAAGCCAC ATAGCTGGGG GGCAGAGG                              38
```

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 7:

CTAAGAGCAA GCCACATAGC TGGGGGGCAG AGG                            33

(2) INFORMATION FOR SEQ ID NO: 8:

(i) SEQUENCE CHARACTERISTICS:
        (A) LENGTH: 41 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 8:

AGTCACTAGG GGTCCAGGTC GCTAGGCGTC AGCAGCGACA C                    41

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 9:

CTGGGGGTCC AGGTCGCTAG GCGTCAGCAG CGACAC                          36

(2) INFORMATION FOR SEQ ID NO: 10:

(i) SEQUENCE CHARACTERISTICS:
        (A) LENGTH: 43 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 10:

TCGAGCTCGG TACCGAGCCC AAATCGGCCG ACAAAACTCA CAC                  43

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 11:

GTACTGCTCC TCCCGCGGCT TTGTCTTG                                      28

(2) INFORMATION FOR SEQ ID NO: 12:

(i) SEQUENCE CHARACTERISTICS:
        (A) LENGTH: 27 base pairs

-continued

```
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 12:

AATTCGGTTA CCTGCAGATA TCAAGCT                                              27

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: unknown
        (D) TOPOLOGY: Not Relevant (ii) MOLECULE TYPE: cDNA (xi) SEQUENCE DESCRIPTION: SEQ ID NO: 13:

AATTAGCTTG ATATCTGCAG GTAACCG                                              27
```

ERYTHROPOIETIN RECEPTOR ANTIBODIES

CROSS REFERENCE TO RELATED APPLICATIONS

This is a national stage filing under 35 U.S.C. §371 of PCT/US96/09613 filed Jun. 7, 1996, which is a continuation-in-part of application Ser. No. 08/474,673 filed Jun. 7, 1995, now abandoned.

FIELD OF THE INVENTION

The present invention relates generally to the generation of monoclonal antibodies by use of a selected antigen: and more particularly to the generation of monoclonal antibodies which are receptor agonists.

BACKGROUND OF THE INVENTION

A vast majority of receptors of the single transmembrane class respond to ligand binding by some form of aggregation. This aggregation can be between identical receptor subunits (as in homodimerization, homotrimerization, etc.) or between different receptor subunits (as is heterodimerization, heterotrimerization, etc). This aggregation appears to be part of the signal for the target cell to respond biologically, in that mutants of the ligand which are unable to interact with the second subunit are still able to bind, but no longer cause dimerization and biological activation of the receptor [P. R. Young, Curr. Opin. Biotech., 3:408–421 (1992)].

For example, there is evidence in the literature that suggests dimerization of the erythropoietin receptor (EpoR) upon ligand binding [S. S. Watowich et al., Molec. Cell Biol., 14:3535–3549 (1992) and S. S. Watowich et al., Proc. Natl. Acad. Sci., USA, 89:2140–2144 (1992)]. Reports about IL-6 have indicated that its second subunit gp130 may dimerize upon IL-6 binding [M. Murkami et al., Science, 260:1808–1810 (1993)]. for some receptors in which homodimerization is induced by ligand binding, monoclonal antibodies (mAbs) were discovered which had agonist properties. These include mAbs to EGF, TNF and growth hormone receptors [A. B. Schrieber et al., J. Biol. Chem., 258:846–853 (1983); L. H. K. Defize et al., EMBO J., 5:1187–1192 (1986); H. Engelmann et al., J. Biol. Chem., 265:14497–14505 (1990); and G. Fuh et al., Science, 256:1677–1680 (1992)]. In each case, these mAbs, by virtue of their two antigen recognition sites, were able to bring together two receptors and thus activate them. Fab fragments made from these mAbs were inactive. In some cases, the apparent affinity of the antibody for receptor was comparable to that of the ligand, e.g., growth hormone [Fuh et al., cited above].

It has also been discovered that antibodies to IL-3 receptor have agonist properties [Suguwara et al., J. Immunol., 140:526–530 (1988)]. Previous literature has described the production of anti-erythropoietin receptor antibodies [A. D'Andrea et al., Blood, 82:46–52 (1993); A. D'Andrea et al., Blood, 84:1982–1991 (1994) and M-G Yet et al., Blood, 82: 1713–1719 (1993). See also, PCT Application WO96/03438 published Feb. 8, 1996. While the Yet et al., reference suggests the occurrence of possible EPO-like activity in one mAb, the mAb is not characterized. Neither Yet et al., nor the other literature provides any reproducible manner of generating agonist mAbs.

There remains a need in the art for the development of additional mAbs which have an affinity for receptors comparable to that of the ligand, and which can act as agonists of the receptor.

SUMMARY OF THE INVENTION

In one aspect, the present invention provides a method for reliably generating an antibody which is an agonist of a receptor. This method employs as the immunizing antigen, a recombinant immunogen which consists of a first extracellular domain of a receptor molecule spaced apart from a second extracellular domain from that receptor by a bridging moiety. The bridging moiety places the first domain and the second domain into a functional proximity which mimics the functional domain orientation and proximity of the naturally occurring multimeric receptor. The bridging moiety can be an amino acid spacer peptide, an organic molecule, an Fe portion of a human immunoglobulin or an amphipathic helix, for example.

In another aspect, the invention includes antibodies produced by the above-described method. The antibodies so generated are characterized by the ability to bind to the naturally occurring receptor and by such binding initiate the biological activity of the receptor. The antibodies of the invention may be chimeric antibodies, humanized antibodies, monoclonal antibodies or polyclonal antibodies.

In still another aspect, the invention provides a recombinant polynucleotide sequence comprising a nucleotide sequence encoding the extracellular domain of a receptor molecule fused in frame to a nucleotide sequence encoding a specific proteolytic cleavage site, said cleavage sequence associated with a bridging moiety.

Yet a further aspect of the invention is the recombinant multimeric immunogen itself.

Additional aspects of this invention include a vector comprising a polynucleotide sequence described above under the control of suitable regulatory sequences capable of directing replication and expression of the polynucleotide sequence in a host cell, and a transformed host cell.

Still other aspects of the invention include therapeutic reagents comprising the antibodies produced by the method of this invention, as well as a method of treating a disease condition by administering a pharmaceutical composition of the invention.

Other aspects and advantages of the present invention are described further in the following detailed description of the preferred embodiments thereof.

BRIEF DESCRIPTION OF THE DRAWINGS

FIGS. 7A–7F is the DNA sequence [SEQ ID NO: 1] for plasmid mtalsEpoRFc containing the sequence encoding the EpoRFc fusion protein under control of a Drosophila S2 mtn promoter. Nucleotides 1 to 897 contain the promoter sequence. The EpoRFc fusion protein [SEQ ID NO: 2] is encoded by the following: nucleotides 898 to 1647 encode the EpoR extracellular domain protein; nucleotides 1648 to 1659 encode the Factor Xa cleavage sequence; nucleotides 1660 to 2361 encoding the human IgG$_1$ Fc sequence. The remainder of the sequence is derived from the plasmid parent. See Example 1.

FIGS. 8A–8E is the DNA sequence [SEQ ID NO: 3] of CosFcLink vector from which a KpnI/XbaI insert containing the IgG1 Fc region was obtained.

DETAILED DESCRIPTION OF THE INVENTION

Figure 1:
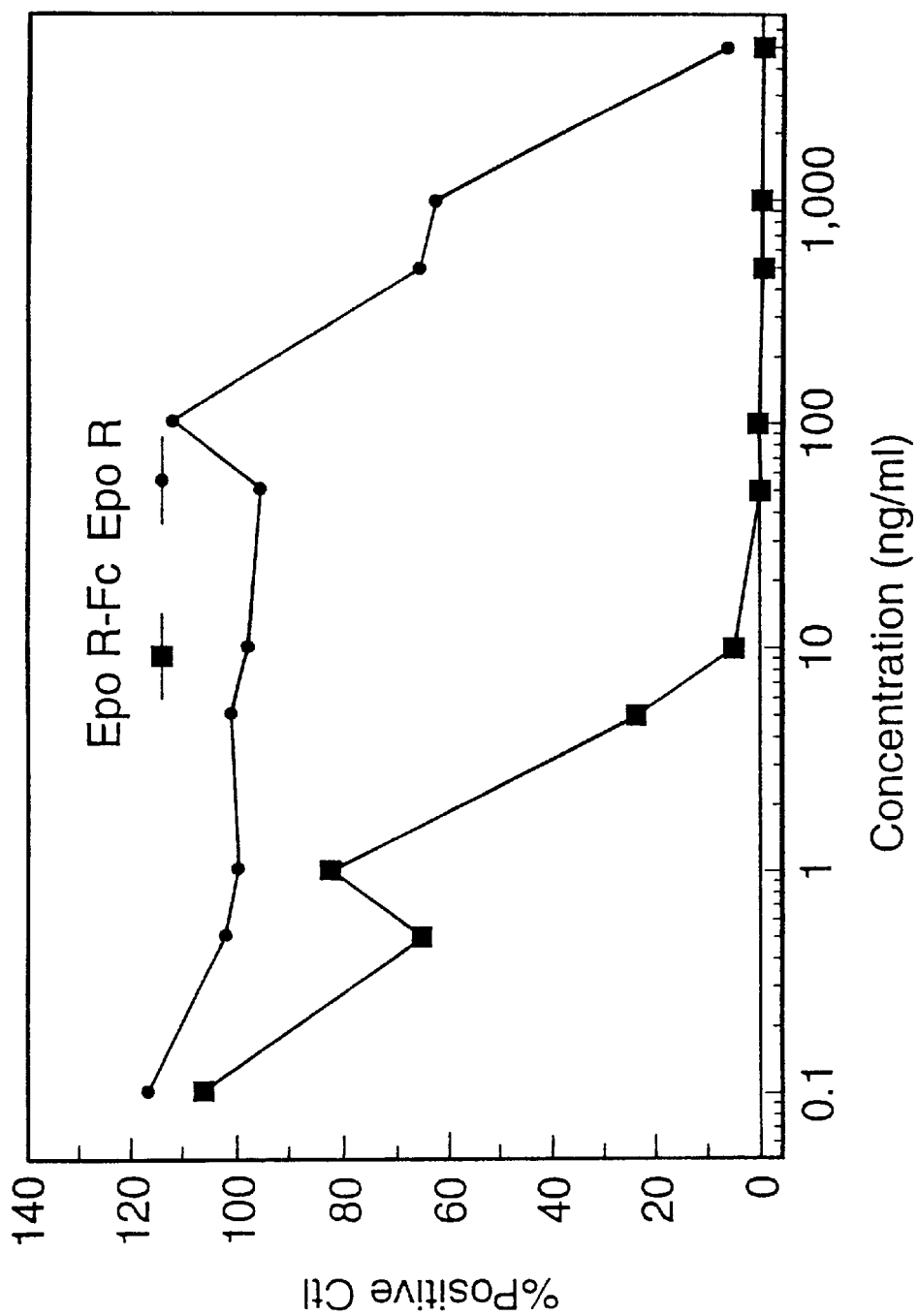
FIG. 1 is a graph illustrating the effects of the dimeric fusion protein EpoRFc and the monomeric protein mEpoR on erythropoietin stimulation of UT-7 Epo cells, which plots % positive control vs. concentration (ng/ml).

The present invention provides a reproducible and reliable composition and method for generating antibodies which demonstrate the agonist properties of the naturally occurring ligand of a receptor molecule. While, in principle, any purified preparation could be used to generate antibodies to a receptor, and from these some may be agonists, this invention provides a specific immunogen which corresponds to a multimeric form of a receptor in which the extracellular domains are in a similar disposition to that expected for receptors having two or more subunits on the surface of the cell.

I. The Recombinant Immunogen

The recombinant immunogen of the present invention consists of an extracellular domain of a selected receptor molecule which is involved in ligand binding via the interaction of more than one extracellular domain. The extracellular domain is spaced apart from a second extracellular receptor domain by a bridging moiety.

By "extracellular domain" is meant that portion of a receptor protein which is localized on the extracellular surface of a cell and which contributes to interaction and binding with its native ligand.

The receptor subunit which contributes the extracellular domain(s) of the immunogen may be any receptor subunit which accomplishes ligand binding via a homodimer of the extracellular domain, a heterodimer of two different subunits of the receptor's extracellular domain, or a multimer of subunits. Receptors which homodimerize upon ligand binding and thus may contribute extracellular domains to the recombinant immunogen include those for, inter alia, erythropoietin (EPO) and thrombopoietin (CMPL), G-CSF, M-CSF, TGF-a, EGF, neu, growth hormone, prolactin, placental lactogen, c-kit (stem cell factor receptor), p50 and p75 receptor subunits of TNFa, and TNFβ. Other receptors which are anticipated to dimerize based on homology to TNF and which can be included in this list are Fas, CD40, CD27, CD30, 4-1BB and OX40.

Similarly, receptors which are already in a homodimeric form on the cell surface, prior to ligand binding may also contribute the extracellular domain(s) to the immunogen. These latter receptors include, inter alia, insulin, IGF1 and IGF2, and PDGF. PDGF includes dimeric ligand made of two chains A and B and two receptor subunits a and b. Ligands and receptors can associate as homo- or heterodimers. Relaxin is also anticipated to be a dimeric receptor prior to ligand binding based on its homology to insulin and IGF.

Receptors which are formed by heterodimers of two different subunits may also be employed as contributors of extracellular domain(s) of one or both of the subunits to the recombinant. Such receptors include, inter alia, GM-CSF, IL-3, IL-5, IL-6, Oncostatin M, CNTF, LIF, NGF, FGF, IL-4, IL-13, IFNa, IFNβ, IFNg, TGFβ1, TGFβ2 and IL-12. Receptors, such as IL-3, which involve more than one subunit may respond to this method, if dimerization of one of the subunits is required for signal transduction.

Receptors which form other aggregations, such as trimers of IL-2 receptor subunits, may also be used as sources of extracellular domain(s) for the recombinant immunogen of this invention.

The extracellular domains of the selected receptor useful in the recombinant immunogen may be isolated and/or otherwise obtained by resort to the published and publicly available receptor sequences. Methods conventional in the art may be employed to isolate or synthesize the appropriate nucleotide sequences encoding these domains for further manipulation in the generation of the immunogen of this invention.

By the term "bridging moiety" is meant a peptide or non-peptide sequence that stably associates with itself and places the first extracellular domain and the second extracellular domain into functional proximity (i.e., a relationship between the two or more domains which mimics the three dimensional functional proximity of the domains in the naturally occurring multimeric receptor, during or prior to ligand binding. Preferably, the bridging moiety is of a sufficient size to bring together the membrane proximal regions (i.e., the regions closes to the transmembrane region) of the extracellular domain. The precise dimensions of the bridging region can be estimated from the relevant crystal structures, such as those for growth hormone and its receptor, or TNF and its receptor [see, e.g., DeVos et al., *Science,* 255:306 (1992)].

The suitability of a given "bridging moiety" can sometimes be evaluated empirically. For example, a dimeric form of a receptor which dimerizes upon binding of ligand is expected to have a higher affinity for ligand than a monomeric form of the extracellular domain of the receptor, if the bridging group is appropriate. This would be evidenced either by direct binding studies of ligand to monomeric and dimeric receptor, or by the relative ability of the two forms of receptor to neutralize the biological activity of the ligand. For example, FIG. 1 shows the ability of dimeric EpoRFc to neutralize Epo activity about 100 times more effectively than monomeric EpoR.

An example of a bridging moiety is an amino acid spacer sequence (e.g., between 1 to 10 amino acids in length and optionally encoding a cleavage site) fused to a dimerization or oligomerization domain which permits the formation of dimers or oligomers, respectively. In the following example, for instance, a spacer encoding the Factor Xa cleavage site is part of the bridging moiety; and the dimerization domain is the hinge CH2CH3 region of a human IgG1. This IgG component consists of the CH2 and CH3 domains and the hinge region of IgG1 including cysteine residues contributing to inter-heavy chain disulfide bonding, for example residues 11 and 14 of the IgG1 hinge region [see, e.g., B. Frangione, *Nature,* 216: 939–941, (1967)]. Preferably the IgG1 component consists of amino acids corresponding to residues 1-4 and 6-15 of the hinge, 1-110 of CH2 and 1 -107 of CH3 of IgG1 described by J. Ellison et al., *Nucleic Acids Res.,* 10: 4071–4079 (1982). Residue 5 of the hinge is changed from cysteine in the published IgG1 sequence to alanine by alteration of TGT to GCC in the nucleotide sequence.

The bridging moiety can also be an Fc portion of any human immunoglobulin with an intact hinge CH2CH3 region, including those derived from IgG, IgE, IgM, IgA and $IgG_4$. Still another suitable bridging moiety is an amino acid spacer fused to the C terminal domain of the TNF-like receptor of the shope fibroma poxvirus [C. A. Smith al., *BBRC,* 176: 335–342 (1991)]. The bridging moiety may also be an a dimerization domain like an amphipathic helix, such as a leucine zipper [see, e.g., P. Pack et al., *Biochem.,* 31(6): 1579–1584 (Feb. 18, 1992)]. The bridging moiety may also be alkaline phosphatase.

Still other desirable embodiments of the bridging moiety are organic molecules which can functionally associate the receptor extracellular domains as desired. Such organic molecules may be selected from among such molecules known to associate peptide sequences to each other for other biological uses, e.g., bifunctional cross-linkers, such as carbodiimide, glutaraldehyde and DSS, BS3, and other which may be obtained from several commercial sources. However, these associations may require combination with specific target sequences for cross-linking, e.g., an exposed Cys or His for nickel chelate, to achieve the appropriate three dimensional disposition of receptor subunits. Choice of an appropriate cross-linker can be determined by comparison to known crystal structures of homologous receptors.

The suitability of a particular peptide or non-peptide entity as a bridging moiety may be functionally assessed in a receptor ligand binding assay. The suitability of the bridging moiety may be determined if the recombinant immunogen binds the receptor's intended ligand with greater affinity than does the monomeric sequence of the receptor extracellular domain. Ligand binding assays for the selected receptors are known to those of skill in the art and maybe readily selected without undue experimentation. See, for example, the EpoR ligand assays described in Komatsu et al., *Blood,* 82:456–464 (1993); Miura et al., *Mol. Cell. Biol.,* 11:4895–4902 (1991): Witthuhn et al., *Cell,* 74:227–236 (1993).

Another bridging moiety or linker may be prepared by mutagenesis of a receptor in the membrane proximal domain to create unpaired Cys, which can disulfide bond to create a dimeric receptor. Such mutations can be evaluated for appropriateness by observing whether the full length receptor containing such a mutation is able to constitutively activate the ligand's activity upon transfection into suitable target cells (e.g., EpoR mutations) [see, e.g., Watowich et al., *Proc. Natl. Acad. Sci., USA.,* 89:2140–2144 (1992)].

Thus, for example, the bridging moiety of the recombinant immunogen can associate two identical extracellular domains into an immunogen that mimics a homodimeric receptor. Alternately, for example, the bridging moiety can associate two different extracellular domains of subunits of one receptor into an immunogen that mimics a heterodimeric receptor. For example, for the heterodimeric association of different subunits from a heterodimeric receptor, a different bridging moiety could be used for each receptor subunit. The bridging moiety for a heterodimeric receptor is preferably a domain that cannot associate with itself, but which preferentially associates with a second domain. Thus, the first bridging moiety can be a CH1 region of a light chain of a selected immunoglobulin. Its complementary bridging moiety is the CH1 region of the heavy chain of the same immunoglobulin or the entire Fc region including the CH1, hinge, CH2, and CH3 regions of the heavy chain. It is also anticipated that various bridging entities may be employed in preparing other multimeric immunogens, e.g., trimers, by associating three identical domains or three extracellular domains from one, two or three subunits of a single receptor. It is presently preferred to use an Fc portion of an immunoglobulin as a bridging moiety to associate the extracellular receptor domains, as disclosed in Example 1 below.

II. Construction and Preparation of the Recombinant Immunogen

The present invention also provides the nucleic acid sequences encoding the recombinant immunogens described above. The nucleotide sequences encoding the extracellular domains of the receptors useful in the immunogens may be obtained from known receptor sequences by conventional means [see J. Sambrook et al., *Molecular Cloning: A Laboratory Manual,* 2nd ed., Cold Spring Harbor Laboratory (1989)]. For example, the nucleotide sequences which form the immunogen of the invention may be isolated by conventional uses of polymerase chain reaction or conventional genetic engineering cloning techniques. Alternatively, these sequences may be constructed using chemical synthesis techniques.

Optionally, a nucleotide sequence which encodes a peptide sequence which provides an enzymatic cleavage site (of which many are well known in the art) is fused in frame to the extracellular domain nucleotide sequence prior to its association with the dimerization or oligomerization domain of the bridging moiety. This facilitates cleavage of the extracellular domain from the bridging moiety following expression.

According to the invention, the nucleic acid sequences encoding the extracellular domains may be modified as desired. It is within the skill of the art to obtain other polynucleotide sequences encoding these receptor domains useful in the invention. Such modifications at the nucleic acid level include, for example, modifications to the nucleotide sequences which are silent or which change the amino acids, e.g. to improve expression or secretion. Such modifications include amino terminal, carboxy terminal or internal deletions of the nucleotide sequences, as desired.

Where the bridging moiety is an amino acid sequence, the nucleotide sequence encoding it is also obtained conventionally and fused to the extracellular domain sequence directly or via a cleavage site or via additional sequence intended as a spacer. For example, where the bridging moiety is an Fc portion of a human immunoglobulin with intact hinge $CH_2CH_3$ region, the nucleotide sequence encoding the Fc region is obtained from known antibody sequences, prepared by conventional techniques and fused in frame to the receptor sequences or to the sequence providing the enzymatic cleavage site.

To produce recombinant immunogens of this invention, a DNA sequence of the invention encoding the extracellular receptor domain, is fused in frame to an optional cleavage site and further fused to a nucleotide sequence encoding a peptide bridging moiety. Preparation of the nucleic acid sequences may be carried out chemically, enzymatically, or by a combination of the two methods, in vitro or in vivo as appropriate. Thus, the DNA sequences may be prepared by the enzymatic ligation of appropriate DNA fragments, by conventional methods such as those described by D. M.

Roberts et al., *Biochem.,* 24:5090–5098 (1985). The DNA fragments may be obtained by digestion of DNA containing the required sequences of nucleotides with appropriate restriction enzymes, by chemical synthesis, by enzymatic polymerization on DNA or RNA templates, or by a combination of these methods. These methods are generally provided by the commercial supplier of the reagents.

For example, digestion with restriction enzymes may be performed in an appropriate buffer at a temperature of 20–70° C., generally in a volume of 50 ul or less with 0.1–10 ug DNA. Enzymatic polymerization of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10–37° C., generally in a volume of 50 ul or less. Enzymatic ligation of DNA fragments may be carried out using a DNA ligase such as T4 DNA ligase in an appropriate buffer at a temperature of 4° C. to ambient, generally in a volume of 50 ul or less. The chemical synthesis of the DNA sequence or fragments may be carried out by conventional phosphotriester, phosphite or phosphoramidite chemistry, using solid phase techniques such as those described in "Chemical and Enzymatic Synthesis of Gene Fragments—A Laboratory Manual" (ed. H. G. Gassen and A. Lang), Verlag Chemie, Weinheim (1982), or in other scientific publications, for example M. J. Gait el al., *Nucleic Acids Res.,* 10: 6243 (1982) and others. Preferably an automated DNA synthesizer is employed. The DNA sequence is preferably prepared by ligating two or more DNA molecules which together comprise a DNA sequence encoding the compound. The DNA molecules may be obtained by the digestion with suitable restriction enzymes of vectors carrying the required coding sequences or by use of polymerase chain reaction technology. The precise structure of the DNA molecules and the way in which they are obtained depends upon the structure of the desired product. The design of a suitable strategy for the construction of the DNA molecule coding for the recombinant immunogen is a routine matter for one skilled in the art.

Once the nucleotide sequence encoding the recombinant immunogen is designed, it is inserted into a suitable expression system. Systems for cloning and expression of a selected protein in a desired microorganism or cell, including, e.g., *E. coli*, Bacillus, Streptomyces, mammalian, insect, and yeast cells, are known and available from private and public laboratories and depositories and from commerical vendors.

Desirably, a recombinant molecule or vector is constructed in which the polynucleotide sequence encoding the immunogen is operably linked to a heterologous expression control sequence permitting expression of the human protein. Numerous types of appropriate expression vectors are known in the art for eukaryotic (including human) protein expression, by standard molecular biology techniques. Such vectors may be selected from among conventional vector types including mammalian, insects, e.g., baculovirus expression, Drosophila S2 cell, or yeast, fungal, bacterial or viral expression systems. Other appropriate expression vectors, of which numerous types are known in the art, can also be used for this purpose. Methods for obtaining such expression vectors are well-known. See, for example, Sambrook et al., cited above; Miller et al., *Genetic Engineering,* 8:277–298 (Plenum Press 1986) and Johansen et al., *Genes and Develop.,* 3:882–889 (1989)].

Suitable host cells or cell lines for transfection by this method include mammalian cells, such as Human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, and product production and purification are known in the art. [See, e.g., Gething and Sambrook, *Nature,* 293:620–625 (1981), or alternatively, Kaufman et al., *Mol. Cell. Biol.,* 5 (7):1750–1759 (1985 ) or Howley et al., U.S. Pat. No. 4,419,446].

Similarly bacterial cells are useful as host cells for the present invention. For example, the various strains of *E. coli* (e.g., HB101, MC1061, and strains used in the following examples) are well-known as host cells in the field of biotechnology. Various strains of *B. subtilis*, Pseudomonas, Streptomyces, other bacilli and the like may also by employed in this method.

Many strains of yeast cells known to those skilled in the art are also available as host cells for expression of the polypeptides of the present invention. Other fungal cells may also be employed as expression systems. Alternatively, insect cells such as *Spodoptera frugipedera* (Sf9) of Drosophila S2 may be used.

Thus, the present invention provides a method for producing a recombinant novel multimeric receptor immunogen which involves transfecting a host cell with at least one expression vector containing a recombinant polynucleotide as above-described under the control of a transcriptional regulatory sequence, e.g. by conventional means such as electroporation. The transfected host cell is then cultured under suitable conditions that allow expression of the product of the recombinant polynucleotide. During expression, the recombinant multimeric immunogen if formed in the cell by the association of the bridging moiety with itself. The expressed multimeric protein is then recovered, isolated, and optionally purified from the culture medium (or from the cell, if expressed intracellularly) by appropriate means known to one of skill in the art.

To generate a heterodimeric receptor immunogen, a vector is designed as above to carry a first receptor subunit which is fused to, e.g., the CH1 region of the light chain. A vector is also designed to carry the second, different subunit of the receptor fused to e.g., the heavy chain sequence (e.g., CH1 region or the entire Fc region of the same Ig that contributes the light chain CH1, as described above). Alternatively both sequences could be present on a single vector. The vectors are prepared as described above. However, for a heterodimeric receptor immunogen, the host cell must be co-transfected with both receptor-bridging moiety polynucleotide sequences. Expression of both sequences in the host cell causes the light chain CH1 and heavy chain CH1, or light chain CH1 and heavy chain Fc sequences to associate only complementarily (e.g., with each other not with their identical counterparts in the cell). Heterodimeric receptor immunogens are thereby formed in the manner of a "Fab"-like fragment or an antibody-like fragment, respectively.

Once expressed, the recombinant immunogen (e.g., homodimeric or heterodimeric) may be isolated following cell lysis in soluble form, or may be extracted using known techniques, e.g., in guanidine chloride. If the protein is secreted, it can be isolated from culture supernatant and purified. With an Fc bridging moiety, Protein A or Protein G Sepharose may be used to purify the immunogen. Where the immunogen is a receptor subunit sequence fused to a peptide, epitope, a specific monoclonal antibody mAb to the peptide epitope can be used to purify the immunogen.

Another method of producing the novel multimeric receptor immunogen involves directly injecting the monomeric recombinant DNA (as, e.g., "naked DNA") into mice or rabbits intramuscularly. The multimeric receptor thus assembles in vivo, where it acts as an immunogen. See, e.g., Cohen, *Science,* 259:1691–92 (1993); E. F. Fynan et al., *Proc. Natl. Acad. Sci., USA,* 90:11478–11482 (1993).

Association of a nucleotide sequence encoding the selected receptor extracellular domain and its optional cleavage site with a non-peptide bridging moiety may be by conventional covalent or ionic bonds, using conventional chemical linking agents. If the association is non-covalent, then cross-linking must occur wither after purification or in freshly isolated cells prior to purification. Alternatively, the opportunity to cross-link could be enhanced by adding ligand to the receptor sequences to bring them into proximity to each other, and cross-linking agent and bridging moiety, and dissociate ligand by a conventional technique, e.g., low pH. The dimeric receptor could then be purified.

III. The Method of the Invention

The recombinant immunogens of this invention are thus useful as antigens for the development of anti-receptor antisera and antibodies to the multimeric receptor domain immunogen. Specific antisera and polyclonal antibodies may be generated by employing the recombinant multimeric immunogen as an immunogen using known techniques. See, Sambrook, cited above, Chapter 18, generally, incorporated by reference. Additionally, polyclonal antibodies and antisera may be generated to the immunogen formed in vivo following administration of the naked DNA.

The polyclonal antibodies developed in the immunized animal may be isolated from the animal's plasma, peripheral blood or other tissue in a conventional manner. Antibodies thus isolated may be employed in the methods described below for generation of mAbs, humanized and chimeric antibodies of the invention.

For example, monoclonal antibodies of the invention may be produced by conventional methods, including the Kohler and Milstein hybridoma technique, in which spleen cells from an immunized animal are fused with immortalized cells to create hybridoma cell lines which secrete a single mAb. Each hybridoma is then screen with a simple binding assay to detect agonist properties.

Other types of anitbodies may be designed based on the agonist mAbs so identified. For example, recombinant techniques, such as described by Huse et al., *Science,* 246:1275–1281 (1988), or any other modifications thereof known to the art may be employed to generate antibodies. Thus, also encompassed within this invention are methods for generating humanized and chimeric agonist antibodies by employing the CDRs from the agonist antibodies produced as described above. Methods of identifying suitable human framework regions and modifying a mAb of the invention to contain same to produce a humanized or chimeric antibody of the invention, are well known to those of skill in the art. See, e.g., E. Mark and Padlin, "Humanization of Monoclonal Antibodies", Chapter 4, *The Handbook of Experimental Pharmacology,* Vol. 113, The Pharmacology of Monoclonal Antibodies, Springer-Verlag (June, 1994). Other types of recombinantly-designed antibodies are also encompassed by this invention.

As used in this specification and the claims, the following terms are defined as follows:

"Altered antibody" refers to a protein encoded by an altered immunoglobulin coding region, which may be obtained by expression in a selected hose cell. Such altered antibodies are engineered antibodies (e.g., chimeric, humanized, reshaped human or reconstituted human antibodies) or antibody fragments lacking all or part of an immunoglobulin constant region, e.g., Fv, Fab, or F(ab')$_2$ and the like.

"Altered immunoglobulin coding region" refers to a nucleic acid sequence encoding the altered antibody of the invention. When the altered antibody is a "reshaped human antibody", the sequences that encode the complementarity determining regions (CDRs) from a donor human immunoglobulin are individually inserted into a first immunoglobulin partner comprising human variable framework or as components of a variable region gene sequence attached to human constant sequences. If desired, the first immunoglobulin partner is operatively linked to a second fusion partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor human antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. (*Sequences of Proteins of Immunological Interest,* 4th Ed., U.S. Department of Health and Human Services, National Institutes of Health (1987)) disclose rules for locating CDRs. In addition, computer programs are known which are useful for identifying CDR regions/structures.

"Second fusion partner" refers to another nucleotide sequence encoding a protein or peptide to which the first immunoglobulin partner is fused in frame or by means of an optional conventional linker sequence (i.e., operatively linked). Preferably the fusion partner is an immunoglobulin gene and when so, it is referred to as a "second immunoglobulin partner". The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). A second fusion partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab')$_2$ are used with their standard meanings (see, e.g., Harlow et al., *Antibodies A Laboratory Manual,* Cold Spring Harbor Laboratory, (1988)).

As used herein, an "engineered antibody" describes a type of altered antibody, i.e., a full-length synthetic antibody (e.g., a chimeric, reconstituted human, or reshaped human antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by an engineered heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody from a heterologous species.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support resides may be altered to preserve binding affinity (see, e.g., Queen et al., *Proc. Nat'l. Acad. Sci. USA,* 86:10029–10032 (1989), Hodgson et al., *Bio/Technology,* 9:421 (1991).

The term "reconstituted human antibody" refers to an antibody in which a Fab is converted into a full length Mab by cloning the heavy chain of the Fab into a human Ig constant region comprising the hinge region and CH-2 and CH-3 domains. Preferably the constant region is one of the IgG isotypes IgG1–IgG4 or variants thereof such as PE muatations. A reconstituted human antibody also includes variants of the processes, mature $NH_2$ terminal regions of the light or heavy chain are altered to conform with the predicted germ line parent sequence.

The term "donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is 1C8.

The term "acceptor antibody" refers to an antibody (monoclonal, or recombinant) from a source genetically unrelated to to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chain. See, e.g., Kabat et al., *Sequences of Proteins of Immunological Interest*, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By "sharing the antigen binding specificity or neutralizing ability" is meant, for example, that although antibody such as 1C18 may be characterized by a certain level of antigen affinity, a CDR encoded by a nucleic acid sequence of 1C8 in an appropriate structural environment may have a lower, or higher affinity. It is expected that CDRs of 1C18 in such environments will nevertheless recognize the same epitope (s) as in 1C8. A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore (Pharmacia) system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

Also provided by the invention are human antibodies derived from human hybridomas, antibodies obtained by rescue from transgenic mice expressing human Ig domains, and antibodies make in primates. Any other modifications which are known to be useful to prepare mAbs as pharmaceutical agents may also be made to the antibodies of this invention.

Without wishing to be bound by theory, it is anticipated that the recombinant immunogens of this invention have configurations mimicking the form of the multimeric receptor on the cell surface. Thus, these immunogens generate a higher frequency of antibodies which crosslink the multiple receptor subunits in a manner similar to that of the naturally occurring ligand and thereby are more likely than randomly obtained antibodies to be agonists of the receptor.

IV. Utilities

Polyclonal antisera, monoclonal antibodies and other antibodies of this invention, which bind to the novel immunogen as the antigen and can function as agonists are useful in substantially the same manner as is the naturally occurring ligand of the receptor. For example, an agonist antibody developed to the exemplary erythropoietin receptor dimeric fusion protein described in Example 2 may be used in therapeutic, diagnostic and research methods in which the ligand, erythropoietin, is useful. These antibodies may be used as research tools and as components for separation of the receptor proteins from other contaminants of living tissue, for example, are also contemplated for these antibodies.

Agonist antibodies to the receptor would have the same therapeutic utility as the natural ligand, but would have the advantage of longer half-life and hence prolonged activity in vivo. These agonists can thus be employed to activate the biological activity which results from receptor/ligand binding. Thus, these agonist antibodies are useful in the treatment of diseases in which the interaction of the receptor and its ligand is part of a biochemical cascade of events leading to a desired response. The advantages of such agonist antibodies include the ability to administer lower dosages of antibody than ligand, easier and less frequent administration of a pharmaceutic based on the agonist antibody, as well as easier purification. Agonist antibodies may demonstrate a different profile of activity in vivo than the non-agonist antibodies due to a different distribution.

Compositions and methods useful for the treatment of conditions associated with abnormal receptor or ligand levels are provided. The present invention provides pharmaceutical compositions useful in the treatment of: anemia associated with chronic renal failure; anemia associated with AIDS; pre-dialysis patients; patients in need of pre- and/or post surgery hematocrit boosting; cancer patients undergoing hematocrit decreasing radiation or chemotherapy; rheumatoid arthritis and sickle cell anemia. These compositions contain a therapeutically effective amount of an agonist antibody of this invention and an acceptable pharmaceutical carrier. As used herein, the term "pharmaceutical" includes veterinary applications of the invention. The term "therapeutically effective amount" refers to that amount of a receptor agonist antibody, which is useful for alleviating a selected condition. Also provided are compositions and methods for inhibiting receptor activity in order to ameliorate an undesired response.

The receptor agonist antibodies of the invention can be formulated into pharmaceutical compositions and administered in the same manner as described for mature proteins [see, e.g., International Patent Application, Publication No. WO 90/02762 (Mar. 22, 1990)]. These therapeutic compositions of the invention may be administered to mimic the effect of the normal receptor ligand. These compositions may contain a pharmaceutically acceptable carrier. Suitable carries are well known to those of skill in the art and include, for example, saline. Alternatively, such compositions may include conventional delivery systems into which protein of the invention is incorporated. Optionally, these compositions may contain other active ingredients, e.g., chemotherapeutics.

Thus, the invention also provides improved methods of treating a variety of disorders in which receptor/ligand interactions are implicated, e.g., inflammation, autoimmune disorders, etc. For example, an agonist antibody developed to a dimeric EpoR of this invention can be employed to treat acute renal failure, anemia, AIDS, and any disorder which the ligand erythropoietin can be used for treatment, e.g., for cancer chemotherapy. Similarly, an agonist antibody developed to a dimeric TopR receptor may be employed to treat conditions of low platelet count, i.e., patients undergoing chemotherapy for cancer, etc. An agonist antibody developed to the G-CSF dimeric receptor of this invention is useful to stimulate the polymorphonuclear cells, thereby for the treatment of conditions characterized by neutropenia, e.g., cancer chemotherapy, etc.

The invention encompasses methods of administering therapeutically effective amounts of a antibody or pharmaceutical compositions of the invention to a patient. The dose, timing and mode of administration of these therapeutic or gene therapy compositions may be determined by one of skill in the art, and may be less than or equal to the amounts of the ligand known to be administered for similar conditions. Such factors as the disease being treated, the age, physical condition, and the level of the receptor detected by the diagnostic methods described above, may be taken into account in determining the dose, timing and mode of administration of the therapeutic compositions of the invention. Generally, where treatment of an existing disorder is indicated, a therapeutic composition of the invention is preferably administered in a site-directed manner and is repeated as needed. Such therapy may be administered in conjunction with conventional therapies for such conditions.

Generally, an agonist antibody of the invention is administered in an amount between about 0.01 ng/kg body weight to about 1 g/kg and preferably about 0.01 ng/kg to 100 mg/kg per dose. Preferably, these pharmaceutical compositions are administered to human or other mammalian subjects by injection. However, administration may be by any appropriate internal route, and may be repeated as needed, e.g., as frequently as one to three times daily for between 1 day to about three weeks to once per week or once biweekly. Preferably, the agonist antibody is administered less frequently than is the ligand, when it is used therapeutically.

Optionally, the pharmaceutical compositions of the invention may contain other active ingredients or be administered in conjunction with other therapeutics. Suitable optional ingredients or other therapeutics include those conventional for treating conditions of this nature, e.g. other anti-inflammatories, diuretics, and immune suppressants, among others.

According to the methods of this invention, and as described in detail in the following examples, antibodies were generated to the erythropoietin receptor (EpoR), which mimic the agonist properties of erythropoietin. The following examples illustrate the construction and expression of exemplary multimeric receptor proteins of the invention. These examples are illustrate only and do not limit the scope of the invention.

EXAMPLE 1

Multimeric EpoR Antigen

A dimeric antigen of this invention was designed by fusing the extracellular domain of the erythropoietin receptor via an amino acid linker to the Fc portion of a human immunoglobulin, and expressing the fusion protein in a suitable host cell.

Using the following primers sets based on the published nucleotide sequence of EpoR (Jones et al., *Blood,* 76:31–35 (1990)), the extracellular domain of the EpoR was amplified via PCR from a human fetal liver cDNA library (Clontech).

One primer was selected from: 5' GT ATC ATG GAC CAC CTC GGG GCG TCC CTC TGG CCC CAG 3' [SEQ ID NO: 4] AND 5' ATG GAC CAC CTC GGG GCG TCC CTC TGG CCC CAG 3' [SEQ ID NO: 5]. A second primer was selected from: 3' GGA GAC GGG GGG TCG ATA CAC CGA ACG AGA ATC CTG TG 5' [SEQ ID NO: 6] and 3' GGA GAC GGG GGG TCG ATA CAC CGA ACG AGA ATC 5' [SEQ ID NO: 7]; 3' CAC AGC GAC GAC TGC GGA TCG CTG GAC CTG GGG atc act ga 5' [SEQ ID NO:8] and 3' CAC AGC GAC GAC TGC GGA TCG CTG GAC CTG GGG gtc 5' [SEQ ID NO: 9].

The resulting 250 bp DNA fragment so isolated was cloned into the vector PCR2000 (Invitrogen) and sequenced.

The EpoR fragment was found to encode amino acids 1–250 [SEQ ID NO: 2] of the extracellular domain of the human EpoR [Jones et al., cited above; SWISSPROT Accession number P19235].

An SpeI/XbaI fragment was isolated from the PCR2000-derived vector by digestion containing this EpoR insert, nucleotide 898 to 1647 of SEQ ID NO: 1. The insert was then cloned into the Drosophila S2 vector mtaI [see, European Patent No. 290,261 B, published Nov. 9, 1988] at the equivalent linker sites, SpeI and XbaI. The resulting plasmid vector, pS2EpoR contains the EpoR extracellular domain gene insert under the control of the Drosophila copper metallothionein (mtn) promoter [Johansen et al., *Genes and Development,* 3:882–889 (1989); Angelichio et al., *Nucl. Acid Res.,* 19:5037–5043 (1991)].

The plasmid pS2EpoR was digested with BssH2 and XbaI and a C terminal fragment of the EpoR sequence was removed by this digestion. A plasmid containing the whole EpoR gene fused to a bridging moiety was then prepared by cloning the following three fragments:

(1) a large BssH2/XbaI fragment from the above digestion;

(2) a synthetic BssH2/KpnI linker, which spanned nucleotide 1561 to nucleotide 1659 of SEQ ID NO: 1, which encoded the C terminus of the EpoR extracellular domain, aa 22 to 250 of SEQ ID NO: 2, linked in frame to the four amino acid recognition sequence for protease Factor Xa cleavage (IleGluGlyArg) [amino acids 251 to 254 of SEQ ID NO: 2], and (3) a KpnI/XbaI fragment containing the human IgG1 Fc region, spanning nucleotide 1660 to the XbaI site which appears at nucleotides 2371–2376 of SEQ ID NO: 1 [see, also Johansen et al., *J. Biol. Chem.,* 270:9459–9471 (1995)]. This KpnI/XbaI fragment was constructed as follows:

Human IgG1 cDNA encoding CH1, the hinge, CH2 and CH3 described by J. Ellison et al., *Nucleic Acids Res.,* 10: 4071–4079 (1982) was cloned from the human IgG plasma cell leukemia ARH-77 (American Type Tissue Collection), using RT-PCR. This cDNA was fully sequenced to confirm identity with the published sequence [see, International patent publication WO 92/00985]. This sequence was inserted into a pUC18 vector (pUC18-Fc). This vector was digested with KpnI and SacII, deleting the CH1, hinge and part of CH2. The deleted region was replaced with a PCR amplified fragment containing the hinge-CH2 region as follows.

Using the following PCR primers: 5'TCG AGC TCG GTA CCG AGC CCA AAT CGG CCG ACA AAA CTC ACA C 3' [SEQ ID NO: 10] and 5' GTA CTG CTC CTC CCG CGG CTT TGT CTT G 3' [SEQ ID NO: 11], a DNA fragment containing the hinge-CH2 region was amplified from pUC18-Fc, digested with KpnI and SacII, gel purified and cloned back into the KpnI/SacII digested pUC18-Fc vector. The Cys, which occurs at position 230 [Kabat numbering; Kabat et al., "Sequences of Proteins of Immunological Interest, 5th Edition, US Department of Health and Human Services, NIH Publication No. 91-3242 (1991); this is also residue 5 of the hinge of the IgG1 heavy chain; residue 261 of SEQ ID NO: 2] was altered to an Ala through a TGT to GCC substitution in the nucleotide sequence to avoid having the unpaired Cys present which is usually involved in light chain-heavy chain crosslinking.

An altered DNA sequence in one of the PCR primers introduced a unique KpnI site at the 5' end of the hinge. The resulting plasmid was called pUC18Fcmod, and the junctions and PCR amplified region were sequenced for confirmation.

The entire hinge-CH2—CH3 insert in pUC18-Fcmod was removed in a single DNA fragment with KpnI and XbaI, gel purified, and ligated into SFcR1Cos4 cut with KpnI and XbaI to create COSFc. SFcR1Cos4 is a derivative of pST4DHFR [K. Deen et al, *Nature,* 331: 82 (1988)] and contains the soluble Fc receptor type I (sFcR1) inserted between the cytomegalovirus (CMV) promoter and bovine growth hormone (BGH) polyadenylation regions, and also contains the dihydrofolate reductase (DHFR) cDNA inserted between the b-globin promoter and SV40 polyadenylation regions, an SV40 origin of replication, and an ampicillin resistance gene for growth in bacteria.

Cutting the vector with KpnI and XbaI removes the sFcR1 coding region, so that the COSFc vector contains the hinge-CH2—CH3 region inserted between the CMV promoter and BGH polyA regions. The COSFcLink vector was made from COSFc by inserting an oligonucleotide linker at the unique EcoRI site of the vector, which recreates this EcoRI site, and also introduces BstEII, PstI and EcoRV cloning sites. The oligonucleotides used were:

5' AATTCGGTTACCTGCAGATATCAAGCT 3' [SEQ ID NO: 12] and

3' CGGAATCCACGTCTATAGTTCGATTAA 5' [SEQ ID NO: 13].

The junction was sequenced to confirm orientation in the vector. The size of the final vector is 6.37 kb and is reported as SEQ ID NO: 3. The KpnI/XbaI fragment used in the dimeric immunogen described herein was obtained from COSFcLink.

The resulting plasmid DNA construct containing the three fragments described above was called pmtaIsEpoRFc [SEQ ID NOS: 1 and 2]. The plasmid sequence contains the heterologous fusion sequence comprising an intact EpoR extracellular domain encoding amino acids 1–250 of SEQ ID NO: 2 linked via a four amino acid linker (aa 251–254 of SEQ ID NO: 2) to a human IgG1 Fc region (aa 255 to 488 of SEQ ID NO: 2). In the plasmid, the fusion sequence was under the control of the mtn promoter, described above.

Plasmid pmtaIsEpoFc was cotransfected into Drosophila S2 cells with a vector encoding hygromycin resistance [see, EP No. 290,261B, cited above]. Stable co-transfectants were selected in hygromycin, and expression of the EpoR induced by $Cu_2SO_4$ according to published protocols [Johansen et al., cited above; Angelichio et al., cited above].

The co-transfected cells secreted the EpoRFc protein as a dimeric molecule due to the natural affinity of the Fc sequence for itself. Under reducing conditions in SDS-PAGE, the EpoRFc protein ran as a monomer. The dimeric protein was purified from Drosophila medium by passage over a Protein A Sepharose column.

To obtain the monomeric EpoR extracellular protein apart from its Fc fusion, the EpoRFc fusion protein is treated as follows: EpoR-Fc was dialyzed into 20 mM Tris, 100 mM NaCl, 2 mM $CaCl_2$, pH 8. Factor Xa (New England Biolabs) was added at a ratio of 1 mg Factor Xa per 25 mg EpoR-Fc and incubated at 6° C. for 18–20 hours.

The digest was then added to Protein A Sepharose 4 Fast Flow [Pharmacia], washed with 100 mM Tris, pH 8, giving a ratio of 0.5 ml packed resin per mg protein. Following a 90 minute incubation with mixing, at 6° C., the resin was separated from the supernatant by centrifugation. SDS/PAGE and Western blots showed that EpoR, free of Fc, was present in the supernatant. The N-terminal sequence for EpoR was correct. The final product was sterile filtered.

EXAMPLE 2

Erythropoietin Binding Assay

The activity of the dimeric fusion protein EpoRFc and the monomeric single-stranded mEpoR protein cleaved from EpoRFc were tested in various biological assays by their ability to neutralize the activity of erythropoietin (Epo).

A. Inhibition of Epo-induced Proliferation of UT7-Epo Cells

An assay for the measurement of Epo activity on the proliferation of UT7Epo cells, which are dependent on Epo for growth [Komatsu et al., *Blood*, 82:456–464 (1993)] was performed as follows. The Epo used in the experiment is Epogen (2000 U/ml) [Amgen, Thousand Oaks, Calif.], diluted in phosphate buffered saline (PBS) and human serum albumin (HSA) for storage at 4° C. at 200 U/ml. Dilutions of cleaved EpoR or EpoRFc protein samples were made, so that final concentrations ranged from 0.001 to 100 ng/ml.

Samples of either EpoR or EpoRFc were added to wells at 10 ul/well in quadruplicate. Epo (0.2 U/ml) was added to each well. UT7Epo cells ($1 \times 10^5$ cells/ml) were plated at 100 ul/well. After the plates were incubated at 37° C. for three days, 10 ul/well of $^3$H-thymidine (diluted to 100 mCi/ml in IMDM+10% fetal calf serum (FCS)) were added to a final concentration of 10 uCi/ml. Plates were incubated at 37° C. for four hours with $^3$H-thymidine. The 96-well plates were harvested onto glass fiber filters using the Tomtec plate harvester with 10% cold TCA and cold 95% ethanol. Solid scintillant was melted onto the filters and the samples counted. The mean and standard error of quadruplicate samples was determined.

The data were reported as the percent of positive (0.2 U/ml) Epo control and are illustrated in FIG. 1.

B. Inhibition of Epo-induced Proliferation of 32D/Epo wt Cells

Another assay was performed for the measurement of Epo activity on the proliferation of 32D/Epo wt cells (Miura, O. et al., *Mol. Cell. Biol.*, 13:1788–1795 (1993)). 32D/Epo wt is an IL-3 dependent cell line transfected with the human Epo receptor.

Figure 2:
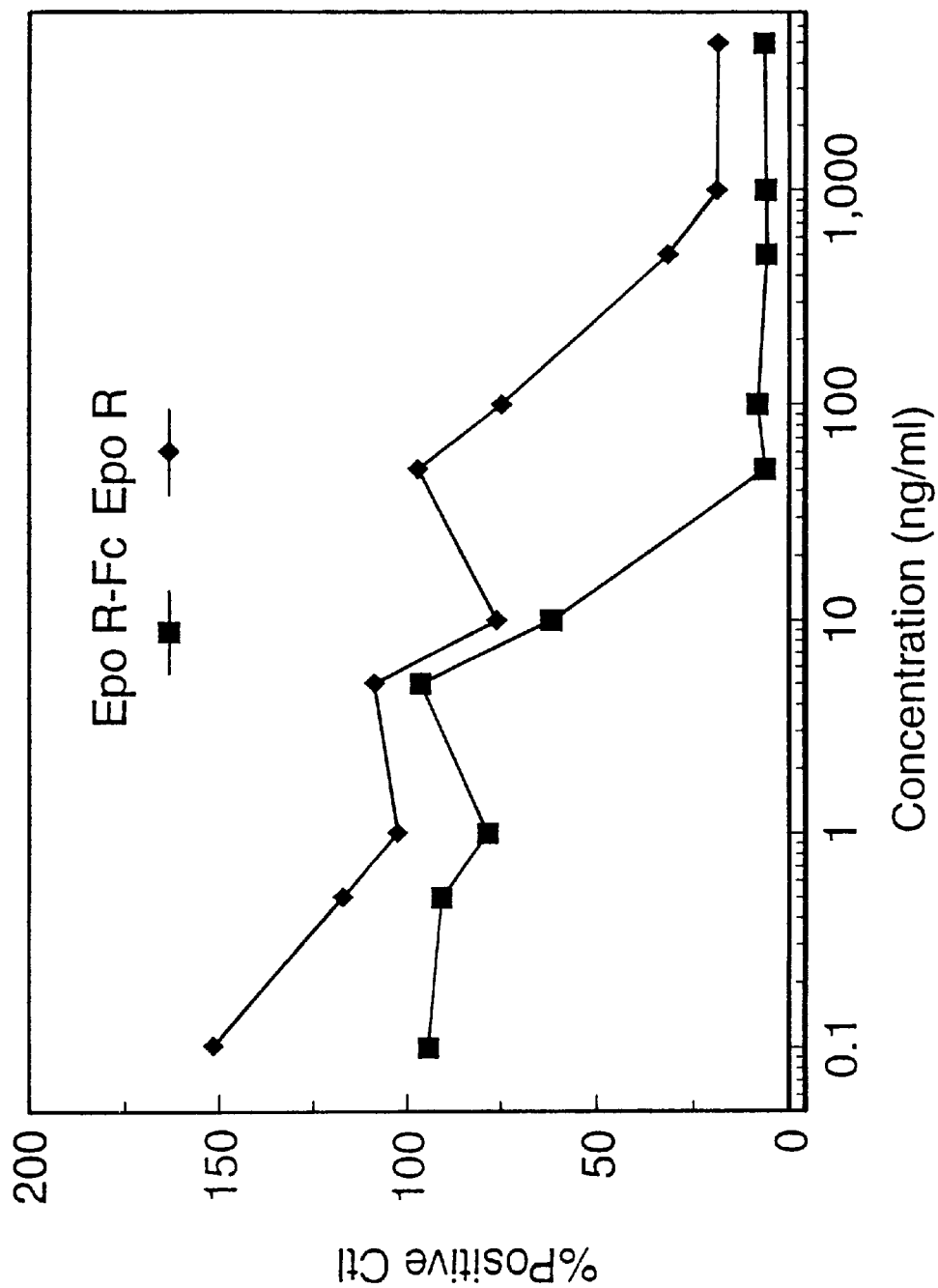
FIG. 2 is a graph illustrating the effects of the dimeric fusion protein EpoRFc and the monomeric protein mEpoR on erythropoietin stimulation of DA3Epowt cells, which plots % positive control vs. concentration (ng/ml).

This assay is performed as described in Part A above, with the modification that the each well contains 1 U/ml Epo. The results of this assay are illustrated in FIG. 2.

C. Inhibition of Epo-induced CFU-E Colony Formation

A third assay for measuring the ability of Epo to stimulate the differentiation of murine bone marrow cells to hemoglobin producing mature erythrocytes (CFU-E assay) was performed as described below.

Murine bone marrow cells were flushed from the femur of female B2D6F1 mice. The marrow cells ($1 \times 10^5$ cells/ml final concentration) were mixed with IMDM, 25% FCS (final) and methylcellulose (0.8% final). 0.4 ml cells was plated per well of 24-well TC plate. EpoRFc (40 ul/well) samples were added and Epo (1 U/ml) was added to each well. Plates were incubated at 37° C., 5% CO2, 6% $O_2$ for two days.

Figure 3:
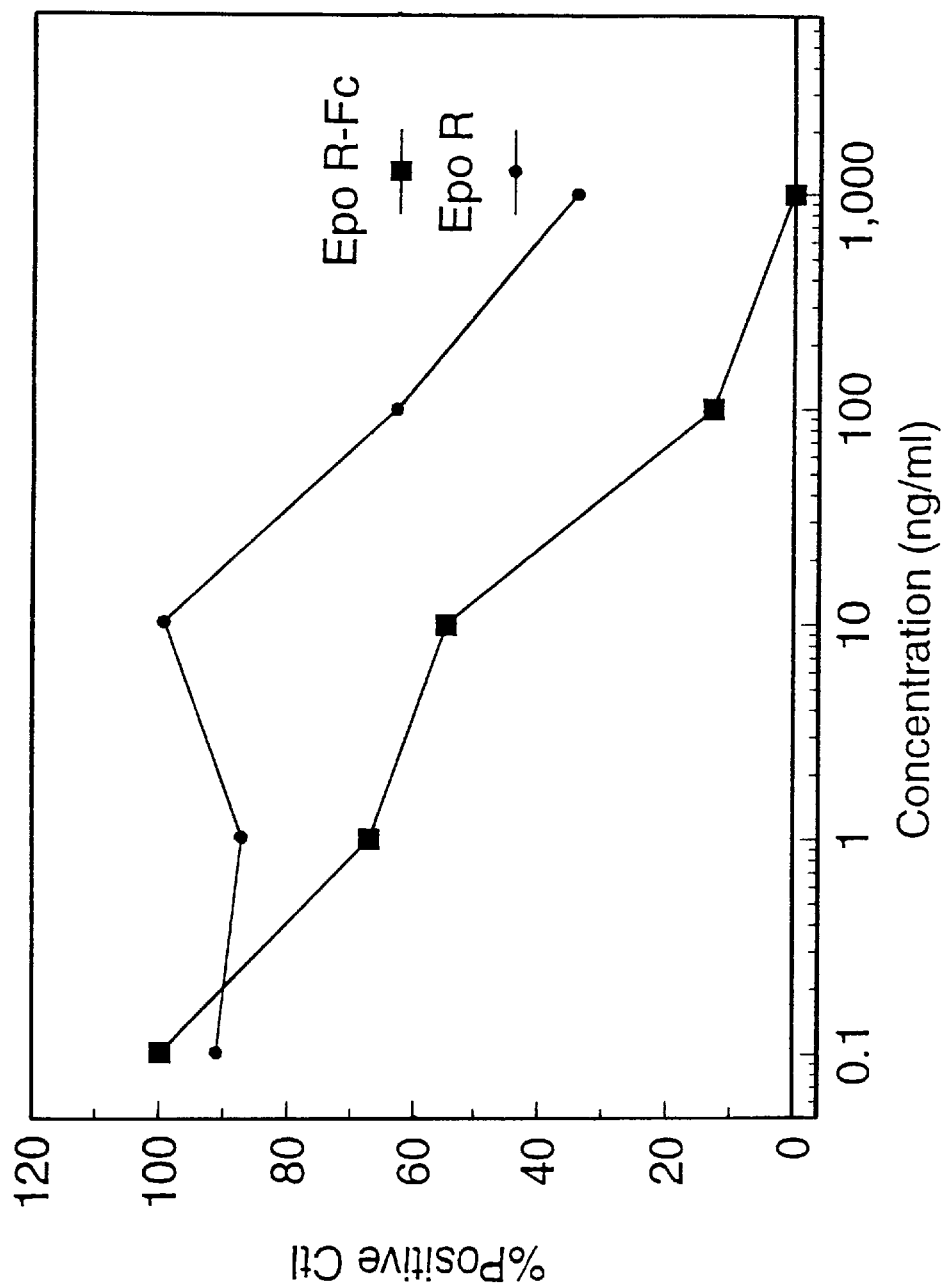
FIG. 3 is a graph illustrating the effects of the dimeric fusion protein EpoRFc and the monomeric protein mEpoR on erythropoietin stimulation in an CFU-E assay, which plots % positive control vs. concentration (ng/ml).

CFU-E colonies containing 8 or more red cells were counted. The mean and standard error of triplicate samples were determined and data reported as the percent of the positive (1 U/ml) Epo control. The results of this assay are illustrated in FIG. 3.

In all three assays, both the monomeric extracellular domain protein EpoR and the dimeric fusion protein EpoRFc were able to bind, and thereby neutralize, the biological activity of the ligand Epo. However, the dimeric fusion protein EpoRFc was consistently 10 to 100 fold more effective at neutralizing Epo activity than non-fused, monomeric extracellular domain protein EpoR, suggesting that the dimeric antigen had a higher affinity to the natural ligand, Epo. The assay results also confirm that the dimeric fusion protein mimics the cell surface form of the natural EpoR in being able to bind to Epo with greater affinity than the mEpoR domain protein.

EXAMPLE 3

Agonist Antibodies of the Invention

A. Generation of Hybridomas

Mice were immunised s.c. with recombinant EpoRFc (34 ug) in Freund's complete adjuvant and then boosted i.p. 4 weeks later (34 ug) with Freund's incomplete adjuvant. One and three days before fusion mice received 20 ug in PBS i.p. The spleens were harvested and fused with myeloma cells according to the method described in Zola. (Monoclonal Antibodies: A Manual of Techniques, Zola H. ed., Boca Raton, Fla.: CRC Press, 1987).

Positive hybridomas were selected through a primary screen described below. Positives were rescreened using a competitive immunoassay and then BIOcore was used to select hybridomas that expressed high affinity monoclonal antibodies which were then cloned twice by the limiting dilution method.

A1. Primary Screening Assay of Anti EpoRFc Hybridomas 96 well microtitre plates were coated with 100 ul/well of EpoRFc at 0.5 ug/ml in coating buffer (50 mM $Na_2HPO_4$, 150 mM NaCl, 0.02% v/v Kathon, pH 7.4) and incubated overnight at 4° C. The well were aspirated and 250 ul/well blocking buffer (1% w/v BSA, 50 mM Tris, 150 mM NaCl, 0.1% v/v Kathon, pH 7.4) added for 1 hour at 37° C. The wells were washed X4 with wash buffer (10 mM Tris, 150 mM NaCl, 0.05% Tween 20, pH 7.4) and 50 ul/well of 40 ug/ml human IgG diluted in assay buffer (0.5% w/v BAS, 0.05% w/v bovine γ globulin, 50 mM Tris, 150 mM NaCl, 7.86 mg/L DTPA, 0.1 g/L Tween-40, 0.02% v/v Kathon, pH 7.4) added followed by 50 ul hybridoma supernatant. The plates were incubated for 1 hour at 37° C. on a plate shaker, the wells washed X4 and then 100 ul/well Europium conjugated anti-mouse IgG added (0.5 ug/ml is assay buffer). After incubation for 1 hour at 37° C. on the plate shaker th wells were again washed X4 and 100 ul/well of enhancement solution added into each well and incubated for 2 min at 22C on the plate shaker and the counts read on a Delfia plate reader.

A2. Isolation of Hybridomas Producing High Affinity Antibodies that Recognise Solution Phase EpoRFc using a Competitive Immunoassay Microtitre plates were coated with EpoRFc and blocked as above. The wells were washed X4 and then 50 ul of either EpoRec at 6 ug/ml diluted in assay buffer or 50 ul human IgG at 40 ug/ml diluted in assay buffer or 50 ul assay buffer alone were added followed by 50 ul hybridoma supernatant. After incubation for 1 hour at 37° C. on the plate shaker the wells were washed X4 followed by addition of 100 ul/well Europium conjugated anti-mouse IgG at 0.5 ug/ml (diluted in assay buffer). After incubation for 1 hour at 37° C. on the plate shaker the well were again washed X4 and 100 ul/well of enhancement solution added into each well and incubated for 2 min at 22° C. on the plate shaker and the counts read on the Delfia plate reader.

Positive antibodies would be displaced by solution phase EpoRFc and these would thus show a reduction in counts when compared to wells with only assay buffer, antibodies giving a reduction in counts with human IgG would be non specific. High affinity antibodies would show >80% reduction in counts.

A hybridoma designated herein as 1C8 (or alternatively as 5-1C8) has been deposited at the European Collection of Animal Cell Cultures, Porton Down, Salisbury, Wiltshire, SP4 OJG United Kingdom on Jun. 5, 1996 and assigned provisional Accession number 69060519. The deposit referred to herein will be maintained under the terms of the Budapest Treaty on the International Recognition of the Deposit of Micro-organisms for purposes of Patent Procedure. These deposits are provided merely as convenience of those of skill in the art and are not an admission that a deposit is required under 35 U.S.C. §112. The sequence of the polynucleotides contained in the deposited material, as well as the amino acid sequence of the polypeptides encoded thereby, are incorporated herein by reference and are controlling in the event of any conflict with any description of sequences herein. A license may be required to make, use or sell the deposited material, and no such license is hereby granted.

A3. Binding analysis in the BIAcore for the Selection of Antibodies that Bound EpoR with High Affinity Rabbit anti-mouse Fc (RAMFc) was immobilised to the sensor chip surface (Pharmacia BIosensor protocol) and used as a capture antibody. The run buffer used was 10 mM HEPES, 150 mM NaCl, 3.4 mM EDTA, 0.005% (v/v) Surfactant P 20 at a flow rate of 5 ul/min. 20 ul hybridoma supernatant was injected over the sensor chip surface followed by 20 ul EpoR or EpoRFc (3 ug/ml diluted in run buffer). The surface was regenerated by injection of 15 ul HCL (100 mM) and then 10 ul SDS (0.025%).

High affinity monoclonal antibodies were selected on the basis of a fast on rate and slow off rate with respect to EpoR binding.

B. Assays to Test Agonist Characteristic of Antibodies

The hybridoma supernatants or purified antibodies were then tested for their ability to bind to the naturally occurring EpoR on UT7 or 32D/Epo wt cells in flow cytometry as follows. $5 \times 10^5$ cells per sample of 32D/Epo wt or UT7-Epo cells were resuspended in 50 ul PBS/10%BSA. 5.0 ul of each purified anti-EpoRFc was diluted to 30 ug/ml and incubated on ice for 45 minutes. Cells were washed and resuspended in 50 ul PBS/10% bovine serum albumin (BSA) and 7 ul FITC-labelled goat anti-mouse IgG (Fab')2 [Tago] added for 45 minutes on ice. Cells were again washed in PBS/10%BSA and resuspended in 0.4 ml PBS/10% BSA and then 0.2 ml 3.2% paraformaldehyde added followed by vortexing. Cells were stored at 4° C. until analysis on Becton-Dickinson's FACScan Fluorescence activated cell sorter.

Figure 4A:
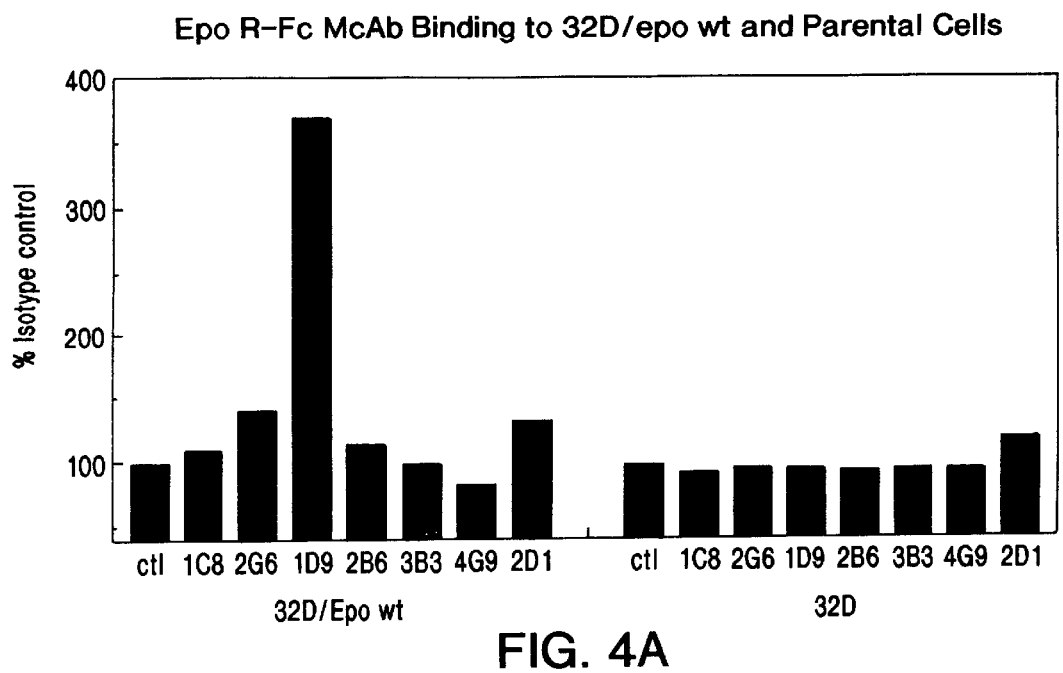
FIGS. 4(A–B) is a bar graph demonstrating the binding of antibodies developed in response to immunization with the EpoRFc fusion protein 32D/Epo wt and parental 32D FIG. (4a) and UT-7EPO, cells, plotting % Isotype control log fluorescence vs. control (CTL) and supernatant designation.
Figure 4B:
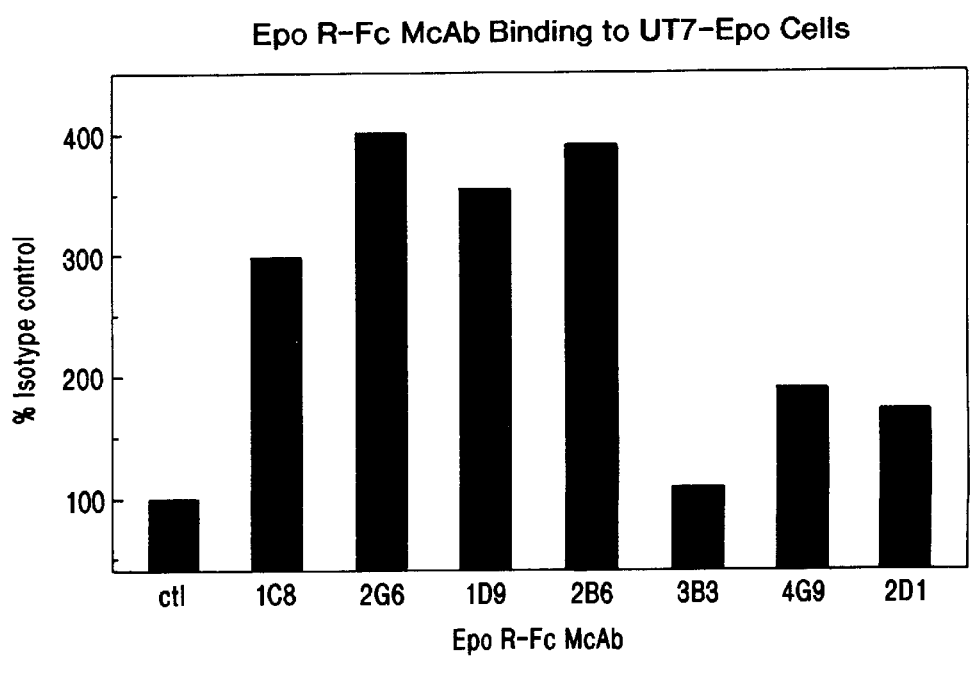

The data, illustrated in FIG. 4, was reported as the % of control antibody fluorescence. As can be seen, four antibodies stained UT7Epo cells while three did not. Interestingly, only one of the four positive antibodies on UT7Epo cells was able to recognize the transfected human Epo receptor in 32D/Epo wt cells, suggesting some differences inthe disposition of the Epo receptor in these cell lines. This also suggests differences in the epitopes recognized by these antibodies.

Figure 5:
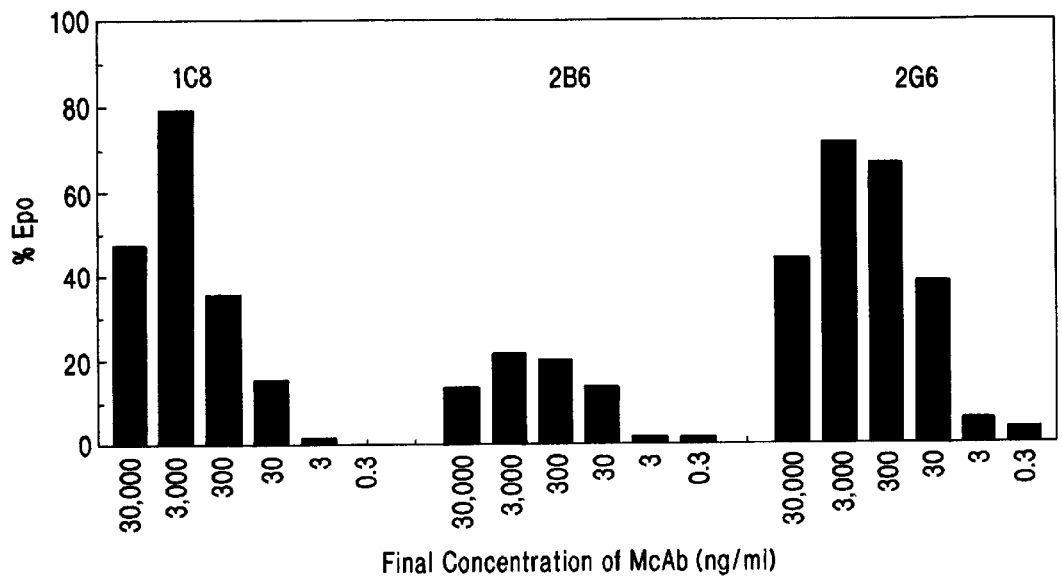
FIG. 5 is a bar graph demonstrating the results of an UT7-EPO proliferation assay with three mAbs to EpoRFc, plotting % Epo maximum vs. dilutions of supernatants. The supernatant designations are listed above the bars.

C. Assays to Test Agonist Activity of Antibodies (1) Hybridoma supernatants or purified antibodies were tested for their ability to mimic the activity of Epo by stimulating the proliferation of UT7-Epo cells in an assay performed as described in Example 2A above, with the modification that Epo is absent from wells containing the hybridoma supernatants. The only sample ws dilutions of the monoclonal antibodies against EpoRFc dimeric protein. Results of this assay are shown in FIG. 5 for some purified EpoR reactive monoclonal antibodies. Four of the antibodies gave significant proliferative activity, in one case approaching that of Epo itself (1C8). The variability of the extent of peak activity relative to Epo suggests that the way in which the antibodies bind may be an important determinant of activity.

(2) Hybridoma supernatants or purified antibodies were tested for their ability to mimic the activity of Epo by stimulating the proliferation and differentiation of human bone marrow progenitor cells to form red blood cell colonies (CFU-E) similar to the assay described above in FIG. 6. The present assay differed in that the progenitor cells were of human origin.

In this procedure, light density cells from human bone marrow centrifuged over Histopaque 1077 were washed and resuspended at $2.5 \times 10^6$ cells/ml in X-vivo medium (BioWhittaker). The purified monoclonal antibodies were diluted in X-vivo medium, and the Epo positive control was 4 U/ml. For the assay, 0.3 ml cells, 0.3 ml Mab sample (or Epo control) and 0.7 ml X-vivo medium were incubated in a polypropylene tube for 30 min at RT, then 0.9 ml FCS, 0.3 ml 10% BSA and 0.8 ml 3.2% methylcellulose were added. 0.4 ml were plated per well of a 24-well TC dish (Nunc.) This procedure departs from the standard assay in the pre-incubation of cells, X-Vivo and Mab alone for 30 min (without serum, BSA or methylcellulose) prior to plating in methylcellulose.

Figure 6:
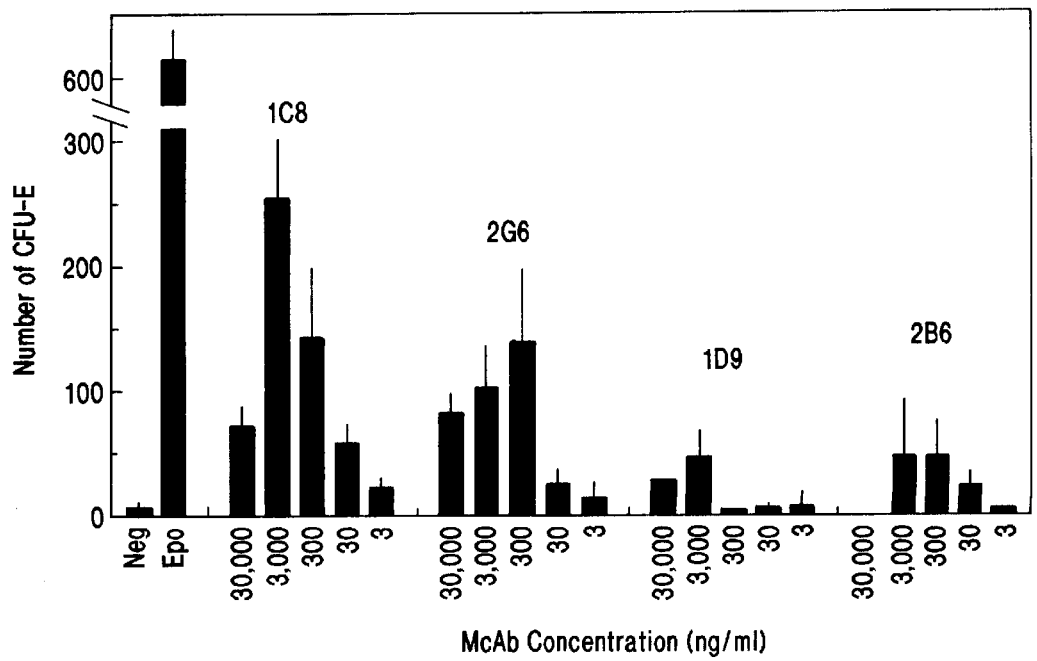
FIG. 6 is a bar graph demonstrating the ability of 4 mAbs to EPORF$_c$ to stimulate the proliferation and differentiation of human bone marrow progenitor cells to form red blood cell colonies (CFU-E), plotting Number of CFU-E vs. positive and negative EPO controls and supernatant dilutions. The supernatant designations are listed above the bars.

The results are shown in FIG. 6. Once again, all four antibodies were positive in the UT7Epo proliferation assay were also able to stimulate the generation of mature red blood cells. Again the most potent was antibody 1C8 which gave almost 50% of the maximal activity of human Epo on the same cells. The order of maximal activity was similar to that observed in the proliferative assay.

D. Epitope Mapping of Agonist Antibodies

It was likely that one contributer to the different activities of the agonist antibodies was the epitope recognized on the erythropoietin receptor. To determine if the antibodies recognized overlapping epitopes on the Epo receptor, the ability of antibodies to compete with each other in binding to EpoR or EpoRFc was measured.

RAMFc was immobilised to the sensor chip surface and using a flow rate of 5 ul/min the following sequential injections were used. 5 ul of first monoclonal antibody (25 or 30 ug/ml), 10 ul EpoR (5 ug/ml) or EpoRFc (6 ug/ml), 2×5 ul of nonspecific monoclonal antibodies, (100 ug/ml each of IgG 2bk, IgG 3k, IgG 1k and IgG 2ak), 5 ul of second monoclonal antibody. The surface was generated with 15 ul 0.1M phosphoric acid and 8 ul 0.025% SDS at 10 ul/min. The data are shown in Table I.

Table I Competition of different monoclonal antibodies for epitopes on Epo receptor as measured by BIAcore. Results are expressed as Response Units. The antibody attached to the chip via protein A is shown in the left hand column and each row shows the binding of each monoclonal after prebinding of EpoR or EpoRFc.

|  | Measurements are in RU | | |
|---|---|---|---|
|  | 5-1C8 | 3-2B6 | 5-2G6 |
| Epo-R |  |  |  |
| 5-1C8 | −25 | −21 | 2 |
| 3-2B6 | −3 | −6 | 269 |
| 5-2G6 | −13 | 169 | — |
| Epo-RFc |  |  |  |
| 5-1C8 | −9.6 | 6.3 | 5.2 |
| 3-2B6 | −7 | −8 | 272 |
| 5-2G6 | −11.6 | 167 | −5 |

The data indicate that of the three agonist antibodies, 2B6 and 2G6 bind to two non-overlapping epitopes since they do not compete for binding to the Epo receptor. In contrast, 1C8 competes with both 2B6 and 2G6, suggesting that it binds to a third distinct epitope which overlaps the other two. Thus there is no single epitope which can lead to agonist activity, but the precise epitope can very likely affect the extent of bioactivity observed. Use of the EpoRFc as antigen seems to generate a wide variety of agonist epitopes.

E. Competition of Antibody Binding with Epo

Another measure of differences between the agonist antibodies is provided by studies which measure the ability of monoclonal antibody to compete with Epo binding to the receptor. These experiments were conducted in two ways. First, a goat anti-human IgG was attached to the BIAcore chip, followed by sequential binding of EpoRFc, Epo and finally monoclonal antibody. In this experiment, pre-binding of Epo blocked the binding of 1C8 by more than 75%, but had only a limited effect on the binding of 1D9, 2G6 and 2B6. Second, if the EpoRFc binding to the chip was followed first by monoclonal antibody and then by Epo, all four monoclonal antibodies could block subsequent binding of Epo. More specifically, a goat anti-human IgG, Fc specific antibody was immobilised on the sensor chip surface. Injection of 25 ul EpoRFc (2 ug/ml) at 5 ul/min was followed by injection of 25 ul Epo (5 ug/ml) then 25 ul Mab (10 ug/ml) at 5 ul/min. RU recorded. The surface was regenerated with injections of 15 ul 0.1M phosphoric acid (5 ul/min) and 8 ul 0.025% SDS at 10 ul/min. and as mentioned above the experiment was repeated reversing the order of addition for EPo and mAB, i.e inject Mab first, then displaced with Epo.

These data, shown in Table II suggest that all four antibodies may block access of Epo to its binding site, but only the 1C8 antibody overlaps substantially with the Epo binding site on the Epo receptor.

Table II Competition of monoclonal antibody binding with Epo binding to Epo receptor as measured by BIAcore. The order to addition is left to right as indicated. The identity of each monoclonal antibody is listed in the left column.

| Mab | EpoRFc + Epo + Mab | | |
|---|---|---|---|
| | EpoR R.U. | Epo R.U. | Mab R.U. |
| Buffer | 557 | 118 | −9.5 |
| 1D9 | 475 | 106 | 173 |
| 2B6 | 471 | 106 | 264 |
| 2G6 | 468 | 104 | 300 |
| 1C8 | 465 | 104 | 77 |

| Mab | EpoR + Mab + Epo | | |
|---|---|---|---|
| | EpoR R.U. | Mab R.U. | Epo R.U. |
| Buffer | 462 | 9.1 | 105 |
| 1D9 | 452 | 173 | 101 |
| 2B6 | 449 | 455 | 9.2 |
| 2G6 | 448 | 474 | 25 |
| 1C8 | 447 | 436 | −196 |

F. Affinity of the Monoclonal Antibodies to the Epo Receptor

The binding kinetics and affinities of the agonist antibodies was determined by measurements in the BIAcore with both the soluble EpoR and with the dimeric EpoRFc. Specifically, RAMFc was immobilised to the sensor chip surface and a flow rate of 5 ul/min was used with run buffer. The Mab was first bound to the RAMFc (5 ul injection) followed by a 20 ul injection of of EpoR (0–4 ug/ml) or EpoRFc (0–6 ug/ml) then buffer flow for 120 sec and regeneration with 15 ul 0.1M phosphoric acid and 8 ul 0.025% SDS at 10 ul/min. The four antibodies showed quite different kinetics and binding constants as listed in Table III.

Table III Affinities and kinetics of binding of monoclonal antibodies to Epo receptor as measured by BIAcore.

| Mab | Kass. $M^{-1} s^{-1}$ | Kdiss. (s) | $K_D$ (M) | (2nd Dissoc. $K_D$) |
|---|---|---|---|---|
| | Binding to Epo-R | | | |
| 1C8 | $2.54 \times 10^5$ | $5.9 \times 10^{-3}$ | $2.3 \times 10^{-8}$ | $4.3 \times 10^{-9}$ |
| 2G6 | $1.64 \times 10^5$ | $4.3 \times 10^{-4}$ | $2.6 \times 10^{-9}$ | |
| 2B6 | $2.4 \times 10^5$ | $1.9 \times 10^{-4}$ | $7.8 \times 10^{-10}$ | |
| | Binding to Epo-RFc | | | |
| 1C8 | $4 \times 10^5$ | N/D | $<5 \times 10^{-10}$ | |
| 2G6 | $1.77 \times 10^5$ | N/D | $<5 \times 10^{-10}$ | |
| 2B6 | $1.96 \times 10^5$ | N/D | $<5 \times 10^{-10}$ | |

N/D No Dissociation

On the monomeric EpoR, the affinities ranged between 0.75 nM and 23 nM. Interestingly, the most biologically potent antibody, 1C8, had the lowest dissociation constant of 23 nM, and also had a second binding mode with a dissociation constant of 4.3 nM. It was only antibody to show this phenomenon. In contrast, with the dimeric receptor EpoRFc, all four antibodies had non-measurable dissociations, suggesting dissociation constants of less than 500 pM. These data suggest that kinetics may also play a role in the relative agonist activity of different monoclonal antibodies.

All documents cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A monoclonal antibody produced by the hybridoma ECACC 96060519.

2. A hybridoma ECACC 96060519.

* * * * *